US010137299B2

United States Patent
Lu et al.

(10) Patent No.: US 10,137,299 B2
(45) Date of Patent: Nov. 27, 2018

(54) ENGAGING THE CERVICAL SPINAL CORD CIRCUITRY TO RE-ENABLE VOLITIONAL CONTROL OF HAND FUNCTION IN TETRAPLEGIC SUBJECTS

(71) Applicant: THE REGENTS OF THE UNIVERSITY OF CALIFORNIA, Oakland, CA (US)

(72) Inventors: Daniel C. Lu, Rancho Palos Verdes, CA (US); V. Reggie Edgerton, Los Angeles, CA (US); Roland R. Roy, Playa Vista, CA (US); Yury P. Gerasimenko, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 42 days.

(21) Appl. No.: 15/025,201

(22) PCT Filed: Sep. 26, 2014

(86) PCT No.: PCT/US2014/057886
§ 371 (c)(1),
(2) Date: Mar. 25, 2016

(87) PCT Pub. No.: WO2015/048563
PCT Pub. Date: Apr. 2, 2015

(65) Prior Publication Data
US 2016/0235977 A1 Aug. 18, 2016

Related U.S. Application Data

(60) Provisional application No. 61/883,694, filed on Sep. 27, 2013.

(51) Int. Cl.
*A61N 1/36* (2006.01)
*A61N 1/05* (2006.01)
(Continued)

(52) U.S. Cl.
CPC ........ *A61N 1/36003* (2013.01); *A61K 31/137* (2013.01); *A61K 31/4168* (2013.01);
(Continued)

(58) Field of Classification Search
CPC ... A61N 1/36; A61N 1/04; A61N 1/05; A61N 1/0551; A61N 1/36014; A61N 1/36067;
(Continued)

(56) References Cited

U.S. PATENT DOCUMENTS 3,543,761 A 12/1970 Bradley
3,662,758 A 5/1972 Glover
(Continued)

FOREIGN PATENT DOCUMENTS

AU 2012204526 A1 7/2013
CA 2 823 592 A1 7/2012
(Continued)

OTHER PUBLICATIONS

U.S. Office Action dated Apr. 8, 2015 issued in U.S. Appl. No. 14/355,812.
(Continued)

*Primary Examiner* — Carl H Layno
*Assistant Examiner* — Jon Eric C Morales
(74) *Attorney, Agent, or Firm* — Tom Hunter; Weaver Austin Villeneuve & Sampson LLP

(57) ABSTRACT

In various embodiments, methods are provided for applying transcutaneous and/or epidural spinal cord stimulation with and without selective pharmaceuticals to restore voluntary control of hand function in tetraplegic subjects.

22 Claims, 12 Drawing Sheets

(51) Int. Cl.
*A61K 31/527* (2006.01)
*A61K 31/137* (2006.01)
*A61K 31/4168* (2006.01)
*A61K 31/4178* (2006.01)
*A61K 31/496* (2006.01)
*A61K 31/4985* (2006.01)
*A61K 31/506* (2006.01)
*A61K 31/517* (2006.01)

(52) U.S. Cl.
CPC ........ *A61K 31/4178* (2013.01); *A61K 31/496* (2013.01); *A61K 31/4985* (2013.01); *A61K 31/506* (2013.01); *A61K 31/517* (2013.01); *A61K 31/527* (2013.01); *A61N 1/0551* (2013.01); *A61N 1/36014* (2013.01); *A61N 1/36067* (2013.01); *A61N 1/36171* (2013.01)

(58) Field of Classification Search
CPC ............ A61N 1/36171; A61N 1/36003; A61K 31/527; A61K 31/137; A61K 31/4168; A61K 31/4178; A61K 31/496; A61K 31/4985; A61K 31/506; A61K 31/517
USPC .......................................................... 607/48
See application file for complete search history.

(56) References Cited

U.S. PATENT DOCUMENTS

| | | |
|---|---|---|
| 3,724,467 A | 4/1973 | Avery et al. |
| 4,044,774 A | 8/1977 | Corbin et al. |
| 4,102,344 A | 7/1978 | Conway et al. |
| 4,141,365 A | 2/1979 | Fischell et al. |
| 4,285,347 A | 8/1981 | Hess |
| 4,340,063 A | 7/1982 | Maurer |
| 4,379,462 A | 4/1983 | Borkan et al. |
| 4,414,986 A | 11/1983 | Dickhudt et al. |
| 4,538,624 A | 9/1985 | Tarjan |
| 4,549,556 A | 10/1985 | Tajan et al. |
| 4,559,948 A | 12/1985 | Liss et al. |
| 4,800,898 A | 1/1989 | Hess et al. |
| 4,934,368 A | 6/1990 | Lynch |
| 4,969,452 A | 11/1990 | Petrofsky et al. |
| 5,002,053 A | 3/1991 | Garcia-Rill et al. |
| 5,031,618 A | 7/1991 | Mullett |
| 5,081,989 A | 1/1992 | Graupe et al. |
| 5,121,754 A | 6/1992 | Mullett |
| 5,344,439 A | 9/1994 | Otten |
| 5,354,320 A | 10/1994 | Schaldach et al. |
| 5,374,285 A | 12/1994 | Vaiani et al. |
| 5,417,719 A | 5/1995 | Hull et al. |
| 5,476,441 A | 12/1995 | Durfee et al. |
| 5,562,718 A | 10/1996 | Palermo |
| 5,643,330 A | 7/1997 | Holsheimer et al. |
| 5,733,322 A | 3/1998 | Starkebaum |
| 5,983,141 A | 11/1999 | Sluijter et al. |
| 6,066,163 A | 5/2000 | John |
| 6,104,957 A | 8/2000 | Alo et al. |
| 6,122,548 A | 9/2000 | Starkebaum et al. |
| 6,308,103 B1 | 10/2001 | Gielen |
| 6,319,241 B1 | 11/2001 | King et al. |
| 6,470,213 B1 | 10/2002 | Alley |
| 6,503,231 B1 | 1/2003 | Prausnitz et al. |
| 6,551,849 B1 | 4/2003 | Kenney |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,819,956 B2 | 11/2004 | DiLorenzo |
| 6,839,594 B2 | 1/2005 | Cohen et al. |
| 6,871,099 B1 | 3/2005 | Whitehurst et al. |
| 6,892,098 B2 | 5/2005 | Ayal et al. |
| 6,895,280 B2 | 5/2005 | Meadows et al. |
| 6,895,283 B2 | 5/2005 | Erickson et al. |
| 6,937,891 B2 | 8/2005 | Leinders et al. |
| 6,950,706 B2 | 9/2005 | Rodriguez et al. |
| 6,975,907 B2 | 12/2005 | Zanakis et al. |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng et al. |
| 7,127,287 B2 | 10/2006 | Duncan et al. |
| 7,127,296 B2 | 10/2006 | Bradley |
| 7,127,297 B2 | 10/2006 | Law et al. |
| 7,153,242 B2 | 12/2006 | Goffer |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen et al. |
| 7,239,920 B1 | 7/2007 | Thacker et al. |
| 7,251,529 B2 | 7/2007 | Greenwood-Van Meerveld |
| 7,252,090 B2 | 8/2007 | Goetz |
| 7,313,440 B2 | 12/2007 | Miesel et al. |
| 7,324,853 B2 | 1/2008 | Ayal et al. |
| 7,330,760 B2 | 2/2008 | Heruth et al. |
| 7,337,005 B2 | 2/2008 | Kim et al. |
| 7,337,006 B2 | 2/2008 | Kim et al. |
| 7,381,192 B2 | 6/2008 | Brodard et al. |
| 7,415,309 B2 | 8/2008 | Mcintyre |
| 7,463,928 B2 | 12/2008 | Lee et al. |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt et al. |
| 7,536,226 B2 | 5/2009 | Williams et al. |
| 7,544,185 B2 | 6/2009 | Bengtsson |
| 7,584,000 B2 | 9/2009 | Erickson |
| 7,590,454 B2 | 9/2009 | Garabedian et al. |
| 7,603,178 B2 | 10/2009 | North et al. |
| 7,628,750 B2 | 12/2009 | Cohen et al. |
| 7,660,636 B2 | 2/2010 | Castel et al. |
| 7,697,995 B2 | 4/2010 | Cross et al. |
| 7,729,781 B2 | 6/2010 | Swoyer et al. |
| 7,734,340 B2 | 6/2010 | De Ridder |
| 7,734,351 B2 | 6/2010 | Testerman et al. |
| 7,769,463 B2 | 8/2010 | Katsnelson |
| 7,797,057 B2 | 9/2010 | Harris |
| 7,801,601 B2 | 9/2010 | Maschino et al. |
| 7,813,803 B2 | 10/2010 | Heruth et al. |
| 7,856,264 B2 | 12/2010 | Firlik et al. |
| 7,877,146 B2 | 1/2011 | Rezai et al. |
| 7,890,182 B2 | 2/2011 | Parramon et al. |
| 7,949,395 B2 | 5/2011 | Kuzma |
| 7,949,403 B2 | 5/2011 | Palermo et al. |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,108,052 B2 | 1/2012 | Boling |
| 8,131,358 B2 | 3/2012 | Moffitt et al. |
| 8,155,750 B2 | 4/2012 | Jaax et al. |
| 8,170,660 B2 | 5/2012 | Dacey, Jr. et al. |
| 8,190,262 B2 | 5/2012 | Gerber et al. |
| 8,195,304 B2 | 6/2012 | Strother et al. |
| 8,229,565 B2 | 7/2012 | Kim et al. |
| 8,239,038 B2 | 8/2012 | Wolf, II |
| 8,260,436 B2 | 9/2012 | Gerber et al. |
| 8,271,099 B1 | 9/2012 | Swanson |
| 8,295,936 B2 | 10/2012 | Wahlstrand et al. |
| 8,311,644 B2 | 11/2012 | Moffitt et al. |
| 8,332,029 B2 | 12/2012 | Glukhovsky et al. |
| 8,346,366 B2 | 1/2013 | Arle et al. |
| 8,352,036 B2 | 1/2013 | DiMarco et al. |
| 8,355,791 B2 | 1/2013 | Moffitt |
| 8,355,797 B2 | 1/2013 | Caparso et al. |
| 8,364,273 B2 | 1/2013 | De Ridder |
| 8,369,961 B2 | 2/2013 | Christman et al. |
| 8,412,345 B2 | 4/2013 | Moffitt |
| 8,428,728 B2 | 4/2013 | Sachs |

(56) References Cited

U.S. PATENT DOCUMENTS

| | | |
|---|---|---|
| 8,442,655 B2 | 5/2013 | Moffitt et al. |
| 8,452,406 B2 | 5/2013 | Arcot-Krishmamurthy et al. |
| 8,588,884 B2 | 11/2013 | Hegde et al. |
| 8,700,145 B2 | 4/2014 | Kilgard et al. |
| 8,712,546 B2 | 4/2014 | Kim et al. |
| 8,750,957 B2 | 6/2014 | Tang et al. |
| 8,805,542 B2 | 8/2014 | Tai et al. |
| 9,101,769 B2 | 8/2015 | Edgerton et al. |
| 9,205,259 B2 | 12/2015 | Kim et al. |
| 9,205,260 B2 | 12/2015 | Kim et al. |
| 9,205,261 B2 | 12/2015 | Kim et al. |
| 9,272,143 B2 | 3/2016 | Libbus et al. |
| 9,393,409 B2 | 7/2016 | Edgerton et al. |
| 9,415,218 B2 | 8/2016 | Edgerton et al. |
| 2002/0055779 A1 | 5/2002 | Andrews |
| 2002/0111661 A1 | 8/2002 | Cross et al. |
| 2002/0115945 A1 | 8/2002 | Herman et al. |
| 2002/0193843 A1 | 12/2002 | Hill et al. |
| 2003/0032992 A1 | 2/2003 | Thacker et al. |
| 2003/0078633 A1 | 4/2003 | Firlik et al. |
| 2003/0100933 A1 | 5/2003 | Ayal et al. |
| 2003/0220679 A1 | 11/2003 | Han |
| 2003/0233137 A1 | 12/2003 | Paul, Jr. |
| 2004/0039425 A1 | 2/2004 | Greenwood-Van Meerveld |
| 2004/0044380 A1 | 3/2004 | Bruninga et al. |
| 2004/0111118 A1 | 6/2004 | Hill et al. |
| 2004/0122483 A1 | 6/2004 | Nathan et al. |
| 2004/0127954 A1 | 7/2004 | McDonald et al. |
| 2004/0133248 A1 | 7/2004 | Frei et al. |
| 2004/0138518 A1 | 7/2004 | Rise et al. |
| 2005/0004622 A1 | 1/2005 | Cullen et al. |
| 2005/0070982 A1 | 3/2005 | Heruth et al. |
| 2005/0075669 A1 | 4/2005 | King |
| 2005/0075678 A1 | 4/2005 | Faul |
| 2005/0102007 A1 | 5/2005 | Ayal et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0209655 A1 | 9/2005 | Bradley et al. |
| 2005/0246004 A1 | 11/2005 | Cameron et al. |
| 2006/0003090 A1 | 1/2006 | Rodger et al. |
| 2006/0041295 A1 | 2/2006 | Osypka |
| 2006/0089696 A1 | 4/2006 | Olsen et al. |
| 2006/0100671 A1 | 5/2006 | Ridder |
| 2006/0111754 A1 | 5/2006 | Rezai et al. |
| 2006/0122678 A1 | 6/2006 | Olsen et al. |
| 2006/0142816 A1 | 6/2006 | Fruitman et al. |
| 2006/0142822 A1 | 6/2006 | Tulgar |
| 2006/0149337 A1 | 7/2006 | John |
| 2006/0239482 A1 | 10/2006 | Hatoum |
| 2007/0016097 A1 | 1/2007 | Farquhar et al. |
| 2007/0016266 A1 | 1/2007 | Paul, Jr. |
| 2007/0049814 A1 | 3/2007 | Muccio |
| 2007/0055337 A1 | 3/2007 | Tanrisever |
| 2007/0060954 A1 | 3/2007 | Cameron et al. |
| 2007/0060980 A1 | 3/2007 | Strother et al. |
| 2007/0073357 A1 | 3/2007 | Rooney et al. |
| 2007/0083240 A1 | 4/2007 | Peterson et al. |
| 2007/0156179 A1 | 7/2007 | Karashurov |
| 2007/0168008 A1 | 7/2007 | Olsen |
| 2007/0179534 A1 | 8/2007 | Firlik et al. |
| 2007/0191709 A1 | 8/2007 | Swanson |
| 2007/0208381 A1 | 9/2007 | Hill et al. |
| 2007/0233204 A1 | 10/2007 | Lima et al. |
| 2007/0255372 A1 | 11/2007 | Metzler et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2008/0021513 A1 | 1/2008 | Thacker et al. |
| 2008/0046049 A1 | 2/2008 | Skubitz et al. |
| 2008/0051851 A1 | 2/2008 | Lin |
| 2008/0071325 A1 | 3/2008 | Bradley |
| 2008/0103579 A1 | 5/2008 | Gerber |
| 2008/0140152 A1 | 6/2008 | Imran et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183224 A1 | 7/2008 | Barolat |
| 2008/0207985 A1 | 8/2008 | Farone |
| 2008/0215113 A1 | 9/2008 | Pawlowicz |
| 2008/0221653 A1 | 9/2008 | Agrawal et al. |
| 2008/0228250 A1 | 9/2008 | Mironer |
| 2008/0234791 A1 | 9/2008 | Arle et al. |
| 2008/0279896 A1 | 11/2008 | Heinen et al. |
| 2009/0012436 A1 | 1/2009 | Lanfermann et al. |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0157141 A1 | 6/2009 | Chiao et al. |
| 2009/0198305 A1 | 8/2009 | Naroditsky et al. |
| 2009/0204173 A1 | 8/2009 | Fang et al. |
| 2009/0270960 A1 | 10/2009 | Zhao et al. |
| 2009/0281599 A1 | 11/2009 | Thacker et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0023103 A1 | 1/2010 | Elborno |
| 2010/0042193 A1 | 2/2010 | Slavin |
| 2010/0070007 A1 | 3/2010 | Parker et al. |
| 2010/0114239 A1 | 5/2010 | McDonald et al. |
| 2010/0125313 A1 | 5/2010 | Lee et al. |
| 2010/0137938 A1 | 6/2010 | Kishawi et al. |
| 2010/0145428 A1 | 6/2010 | Cameron et al. |
| 2010/0152811 A1 | 6/2010 | Flaherty |
| 2010/0185253 A1 | 7/2010 | Dimarco et al. |
| 2010/0198298 A1 | 8/2010 | Glukhovsky et al. |
| 2010/0217355 A1 | 8/2010 | Tass et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0305660 A1 | 12/2010 | Hegi et al. |
| 2010/0318168 A1 | 12/2010 | Bighetti |
| 2010/0331925 A1 | 12/2010 | Peterson |
| 2011/0029040 A1 | 2/2011 | Walker et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054579 A1 | 3/2011 | Kumar et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0160810 A1 | 6/2011 | Griffith |
| 2011/0166546 A1 | 7/2011 | Jaax et al. |
| 2011/0184488 A1 | 7/2011 | De Ridder |
| 2011/0184489 A1 | 7/2011 | Nicolelis et al. |
| 2011/0218594 A1 | 9/2011 | Doran et al. |
| 2011/0224665 A1 | 9/2011 | Crosby et al. |
| 2011/0224753 A1 | 9/2011 | Palermo et al. |
| 2011/0224757 A1 | 9/2011 | Zdeblick et al. |
| 2011/0230701 A1 | 9/2011 | Simon et al. |
| 2011/0245734 A1 | 10/2011 | Wagner et al. |
| 2011/0276107 A1 | 11/2011 | Simon et al. |
| 2012/0006793 A1 | 1/2012 | Swanson |
| 2012/0029528 A1 | 2/2012 | Macdonald et al. |
| 2012/0035684 A1 | 2/2012 | Thompson et al. |
| 2012/0101326 A1 | 4/2012 | Simon et al. |
| 2012/0109251 A1 | 5/2012 | Lebedev et al. |
| 2012/0109295 A1 | 5/2012 | Fan |
| 2012/0123293 A1 | 5/2012 | Shah et al. |
| 2012/0165899 A1 | 6/2012 | Gliner |
| 2012/0172946 A1 | 7/2012 | Altaris et al. |
| 2012/0179222 A1 | 7/2012 | Jaax et al. |
| 2012/0185020 A1 | 7/2012 | Simon et al. |
| 2012/0232615 A1 | 9/2012 | Barolat et al. |
| 2012/0252874 A1 | 10/2012 | Feinstein et al. |
| 2012/0259380 A1 | 10/2012 | Pyles |
| 2012/0277824 A1 | 11/2012 | Li |
| 2012/0277834 A1 | 11/2012 | Mercanzini et al. |
| 2012/0283697 A1 | 11/2012 | Kim et al. |
| 2012/0283797 A1 | 11/2012 | De Ridder |
| 2012/0310305 A1 | 12/2012 | Kaula et al. |
| 2012/0330391 A1 | 12/2012 | Bradley et al. |

(56) References Cited

U.S. PATENT DOCUMENTS

| | | |
|---|---|---|
| 2013/0013041 A1 | 1/2013 | Glukhovsky et al. |
| 2013/0030319 A1 | 1/2013 | Hettrick et al. |
| 2013/0030501 A1 | 1/2013 | Feler et al. |
| 2013/0066392 A1 | 3/2013 | Simon et al. |
| 2013/0085317 A1 | 4/2013 | Feinstein |
| 2013/0110196 A1 | 5/2013 | Alataris et al. |
| 2013/0123568 A1 | 5/2013 | Hamilton et al. |
| 2013/0165991 A1 | 6/2013 | Kim et al. |
| 2013/0197408 A1 | 8/2013 | Goldfarb et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268021 A1 | 10/2013 | Moffitt |
| 2013/0281890 A1 | 10/2013 | Mishelevich |
| 2013/0303873 A1 | 11/2013 | Voros et al. |
| 2013/0304159 A1 | 11/2013 | Simon et al. |
| 2013/0310911 A1 | 11/2013 | Tai et al. |
| 2014/0031893 A1 | 1/2014 | Walker et al. |
| 2014/0046407 A1 | 2/2014 | Ben-Ezra et al. |
| 2014/0058490 A1 | 2/2014 | DiMarco |
| 2014/0066950 A1 | 3/2014 | Macdonald et al. |
| 2014/0067007 A1 | 3/2014 | Drees et al. |
| 2014/0067354 A1 | 3/2014 | Kaula et al. |
| 2014/0081071 A1 | 3/2014 | Simon et al. |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0163640 A1 | 6/2014 | Edgerton et al. |
| 2014/0180361 A1 | 6/2014 | Burdick et al. |
| 2014/0213842 A1 | 7/2014 | Simon et al. |
| 2014/0236257 A1 | 8/2014 | Parker et al. |
| 2014/0296752 A1 | 10/2014 | Edgerton et al. |
| 2014/0303901 A1 | 10/2014 | Sadeh |
| 2014/0316484 A1 | 10/2014 | Edgerton et al. |
| 2014/0316503 A1 | 10/2014 | Tai et al. |
| 2014/0324118 A1 | 10/2014 | Simon et al. |
| 2014/0330335 A1 | 11/2014 | Errico et al. |
| 2014/0357936 A1 | 12/2014 | Simon et al. |
| 2015/0065559 A1 | 3/2015 | Feinstein et al. |
| 2015/0165226 A1 | 6/2015 | Simon et al. |
| 2015/0182784 A1 | 7/2015 | Barriskill et al. |
| 2015/0231396 A1 | 8/2015 | Burdick et al. |
| 2015/0265830 A1 | 9/2015 | Simon et al. |
| 2016/0030737 A1* | 2/2016 | Gerasimenko ..... A61N 1/36003 607/48 |
| 2016/0030748 A1 | 2/2016 | Edgerton et al. |
| 2016/0045727 A1 | 2/2016 | Rezai et al. |
| 2016/0045731 A1 | 2/2016 | Simon et al. |
| 2016/0121109 A1 | 5/2016 | Edgerton et al. |
| 2016/0121116 A1 | 5/2016 | Simon et al. |
| 2016/0175586 A1 | 6/2016 | Edgerton et al. |
| 2016/0220813 A1 | 8/2016 | Edgerton et al. |
| 2017/0007831 A1 | 1/2017 | Edgerton et al. |
| 2017/0157389 A1 | 6/2017 | Tai et al. |
| 2017/0165497 A1 | 6/2017 | Lu |
| 2017/0246450 A1 | 8/2017 | Liu et al. |
| 2017/0246452 A1 | 8/2017 | Liu et al. |
| 2017/0274209 A1 | 9/2017 | Edgerton et al. |

FOREIGN PATENT DOCUMENTS

| | | |
|---|---|---|
| EP | 2661307 A2 | 11/2013 |
| EP | 2968940 A1 | 1/2016 |
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2001102533 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| WO | WO 97/047357 A1 | 12/1997 |
| WO | WO 03/026735 A2 | 4/2003 |
| WO | WO 03/092795 A1 | 11/2003 |
| WO | WO 2004/087116 A2 | 10/2004 |
| WO | WO 2005/051306 A2 | 6/2005 |
| WO | WO 2005/087307 A2 | 9/2005 |
| WO | WO 2007/107831 A2 | 9/2007 |
| WO | WO 2008/109862 A1 | 9/2008 |
| WO | WO 2008/121891 A1 | 10/2008 |
| WO | WO 2009/042217 A1 | 4/2009 |
| WO | WO 2009/111142 A2 | 9/2009 |
| WO | WO 2010/055421 A1 | 5/2010 |
| WO | WO 2010/114998 A1 | 10/2010 |
| WO | WO 2010/124128 A1 | 10/2010 |
| WO | WO 2012/094346 A2 | 7/2012 |
| WO | WO 2012/100260 A2 | 7/2012 |
| WO | WO 2012/129574 A2 | 9/2012 |
| WO | WO 2013/071307 A1 | 5/2013 |
| WO | WO 2013/071309 A1 | 5/2013 |
| WO | WO 2014/144785 A1 | 9/2014 |
| WO | WO 2015/048563 A2 | 4/2015 |
| WO | WO 2016/029159 A2 | 2/2016 |
| WO | WO 2016/033369 A1 | 3/2016 |
| WO | WO 2016/033372 A1 | 3/2016 |
| WO | WO 2017/011410 A1 | 1/2017 |
| WO | WO 2017/024276 A1 | 2/2017 |
| WO | WO 2017/035512 A1 | 3/2017 |

OTHER PUBLICATIONS

U.S. Final Office Action dated Sep. 21, 2015 issued in U.S. Appl. No. 14/355,812.
U.S. Notice of Allowance dated Apr. 13, 2016 issued in U.S. Appl. No. 14/355,812.
U.S. Office Action dated Oct. 18, 2016 issued in U.S. Appl. No. 15/208,529.
U.S. Final Office Action dated Jul. 13, 2017 issued in U.S. Appl. No. 15/208,529.
U.S. Office Action dated Jul. 13, 2016 issued in U.S. Appl. No. 14/775,618.
U.S. Final Office Action dated Apr. 25, 2017 issued in U.S. Appl. No. 14/775,618.
U.S. Notice of Allowance dated Jan. 18, 2018 issued in U.S. Appl. No. 14/775,618.
PCT International Search Report dated Jul. 30, 2012 issued in PCT/US2012/020112.
PCT International Preliminary Report on Patentability and Written Opinion dated Jul. 10, 2013 issued in PCT/US2012/020112.
PCT International Search Report and Written Opinion dated Mar. 19, 2013 issued in PCT/US2012/064878.
PCT International Preliminary Report on Patentability dated May 22, 2014 issued in PCT/US2012/064878.
Australian Patent Examination Report No. 1 dated Jul. 11, 2016 issued in AU 2012334926.
European Communication pursuant to Rule 114(2) EPC regarding observations by a third party dated Mar. 27, 2015 issued in EP 12 847 885.6.
European Extended Search Report dated May 6, 2015 issued in EP 12 847 885.6.
European Office Action dated Apr. 15, 2016 issued in EP 12 847 885.6.
European Reply to Communication of Apr. 15, 2016 dated Oct. 24, 2016 in EP 12 847 885.6.
European Second Office Action dated Feb. 16, 2017 issued in EP 12 847 885.6.
PCT Declaration of Non-Establishment of International Search Report and Written Opinion dated Dec. 24, 2014 issued in PCT/US2014/057886.

(56) References Cited

OTHER PUBLICATIONS

PCT International Preliminary Report on Patentability and Written Opinion dated Apr. 7, 2016 issued in PCT/US2014/057886.
European Extended Search Report dated May 10, 2017 issued in EP 14849355.4.
PCT International Search Report and Written Opinion dated Aug. 6, 2014 issued in PCT/US2014/029340.
PCT International Preliminary Report on Patentability dated Sep. 24, 2015 issued in PCT/US2014/029340.
European Extended Search Report dated Nov. 8, 2016 issued in EP 14 76 5477.6.
PCT International Search Report and Written Opinion dated Dec. 5, 2016 issued in PCT/US2016/045898.
PCT International Preliminary Report on Patentability and Written Opinion dated Feb. 15, 2018 issued in PCT/US2016/045898.
PCT International Search Report and Written Opinion dated Dec. 8, 2015 issued in PCT/US2015/047268.
PCT International Preliminary Report on Patentability and Written Opinion dated Feb. 28, 2017 issued in PCT/US2015/047268.
European Extended Search Report dated Mar. 1, 2018 issued in EP 15836927.2.
PCT International Search Report and Written Opinion dated Dec. 3, 2015 issued in PCT/US2015/047272.
PCT International Preliminary Report on Patentability and Written Opinion dated Feb. 28, 2017 issued in PCT/US2015/047272.
PCT Declaration of Non-Establishment of International Search Report and Written Opinion dated Dec. 1, 2015 issued in PCT/US2015/046378.
PCT International Preliminary Report on Patentability and Written Opinion dated Feb. 21, 2017 issued in PCT/US2015/046378.
PCT International Search Report and Written Opinion dated Sep. 12, 2016 issued in PCT/US2016/041802.
PCT International Preliminary Report on Patentability and Written Opinion dated Jan. 25, 2018 issued in PCT/US2016/041802.
PCT International Search Report and Written Opinion dated Dec. 5, 2016 issued in PCT/US2016/049129.
PCT International Preliminary Report on Patentability and Written Opinion dated Mar. 8, 2018 issued in PCT/US2016/049129.
PCT International Search Report dated Mar. 19, 2013 issued in PCT/US2012/064874.
PCT International Search Report dated Mar. 19, 2013 issued in PCT/US2012/064878.
PCT International Search Report dated Sep. 3, 2012 issued in PCT/US2012/022257.
PCT International Search Report dated Oct. 31, 2012 issued in PCT/US2012/030624.
Angeli et al. (2014) "Altering spinal cord excitability enables voluntary movements after chronic complete paralysis in humans" *Brain* 137: 1394-1409.
Courtine, Grégoire et al. (2007) "Modulation of multisegmental monosynaptic responses in a variety of leg muscles during walking and running in humans," *J Physiol.* 582.3:1125-1139.
Danner S.M., Hofstoetter U.S., Ladenbauer J., Rattay F., and Minassian K. (Mar. 2011) "Can the human lumbar posterior columns be stimulated by transcutaneous spinal cord stimulation? A modeling study" *Europe PMC Funders Author Manuscripts, Artif Organs* 35(3):257-262, 12 pp.
DeSantana et al. (Dec. 2008) "Effectiveness of Transcutaneous Electrical Nerve Stimulation for Treatment of Hyperalgesia and Pain," *Curr Rheumatol Rep.* 10(6):492-499, 12 pp.
Dubinsky, Richard M. and Miyasaki, Janis, "Assessment: Efficacy of transcutaneous electric nerve stimulation in the treatment of pain in neurologic disorders (an evidence-based review)," Report of the Therapeutics and Technology Assessment Subcommittee of the American Academy of Neurology, (2010) *Neurology*, 74:173-176.
Fong et al. (2009) "Recovery of control of posture and locomotion after a spinal cord injury: solutions staring us in the face," *Progress in Brain Research*, Elsevier Amsterdam, NL,175:393-418.
Ganley et al., (2005) "Epidural Spinal Cord Stimulation Improves Locomoter Performance in Low ASIA C, Wheelchair-Dependent, Spinal Cord-Injured Individuals: Insights from Metabolic Response," *Top. Spinal Cord Inj. Rehabil*;11(2):50-63.
Gerasimenko Y., Gorodnichev R., Machueva E., Pivovarova E., Semyenov D., Savochin A., Roy R.R., and Edgerton V.R., (Mar. 10, 2010) "Novel and Direct Access to the Human Locomotor Spinal Circuitry," *J Neurosci.* 30(10):3700-3708, PMC2847395.
Gerasimenko Y.P., Ichiyama R.M., Lavrov I.A., Courtine G., Cai L., Zhong H., Roy R.R., and Edgerton V.R. (2007) "Epidural Spinal Cord Stimulation Plus Quipazine Administration Enable Stepping in Complete Spinal Adult Rats," *J Neurophysiol.* 98:2525-2536.
Harkema et al. (2011) "Effect of Epidural stimulation of the lumbosacral spinal cord on voluntary movement, standing, and assisted stepping after motor complete paraplegia: a case study" *Lancet* 377(9781): 1938-1947; NIH Public Access Author Manuscript 17 pages [doi:10.1016/S0140-6736(11)60547-3].
Herman R., He J., D'Luzansky S., Willis W., Dilli S., (2002) "Spinal cord stimulation facilitates functional walking in a chronic, incomplete spinal cord injured," *Spinal Cord.* 40:65-68.
Hofstoetter, U.S. et al. (Aug. 2008) "Modification of Reflex Responses to Lumbar Posterior Root Stimulation by Motor Tasks in Healthy Subjects," *Artif Organs*, 32(8):644-648.
Ichiyama et al. (2005) "Hindlimb stepping movements in complete spinal rats induced by epidural spinal cord stimulation" *Neuroscience Letters*, 383:339-344.
Kitano K., Koceja D.M. (2009) "Spinal reflex in human lower leg muscles evoked by transcutaneous spinal cord stimulation," *J Neurosci Methods.* 180:111-115.
Minasian et al. (2010) "Transcutaneous stimulation of the human lumbar spinal cord: Facilitating locomotor output in spinal cord injury," *Conf. Proceedings Soc. For Neurosci.*, Abstract No. 286.19, 1 page.
Minassian et al. (Aug. 2011) "Transcutaneous spinal cord stimulation," *International Society for Restorative Neurology*, http://restorativeneurology.org/resource-center/assessments/transcutaneous-lumbar-spinal-cord-stimulation/; http://restorativeneurology.org/wp-content/upl oads/2011/08/Transcutaneous-spinal-cord-stimulation_long.pdf, 6 pp.
Minassian et al. (Mar. 2007) "Posterior root-muscle reflexes elicited by transcutaneous stimulation of the human lumbosacral cord," *Muscle & Nerve* 35:327-336.
Nandra et al., (2014) "Microelectrode Implants for Spinal Cord Stimulation in Rats," *Thesis, California Institute of Technology*, Pasadena, California, Defended on Sep. 24, 2014, 104 pages.
Nandra et al., (Jan. 23, 2011) "A Parylene-Based Microelectrode Arrary Implant for Spinal Cord Stimulation in Rats," *Conf. Proc. IEEE Eng. Med. Biol. Soc.*, pp. 1007-1010.
Rodger et al., (2007) "High Density Flexible Parylene-Based Multielectrode Arrays for Retinal and Spinal Cord Stimulation," Transducers & Eurosensors, Proc. of the 14th International Conference on Solid-State Sensors, Actuators and Microsystems, Lyon, France, Jun. 10-14, 2007, *IEEE*, pp. 1385-1388.
Seifert et al. (Nov. 1, 2002) "Restoration of Movement Using Functional Electrical Stimulation and Bayes' Theorem," *The Journal of Neuroscience*, 22(1):9465-9474.
Tanabe et al. (2008) "Effects of transcutaneous electrical stimulation combined with locomotion-like movement in the treatment of post-stroke gait disorder: a single-case study," 30(5):411-416 abstract, 1 page.
Ward, Alex R. (Feb. 2009) "Electrical Stimulation Using Kilohertz—Frequency Alternating Current," (2009) *Phys Ther.*89(2):181-190 [published online Dec. 18, 2008].

* cited by examiner

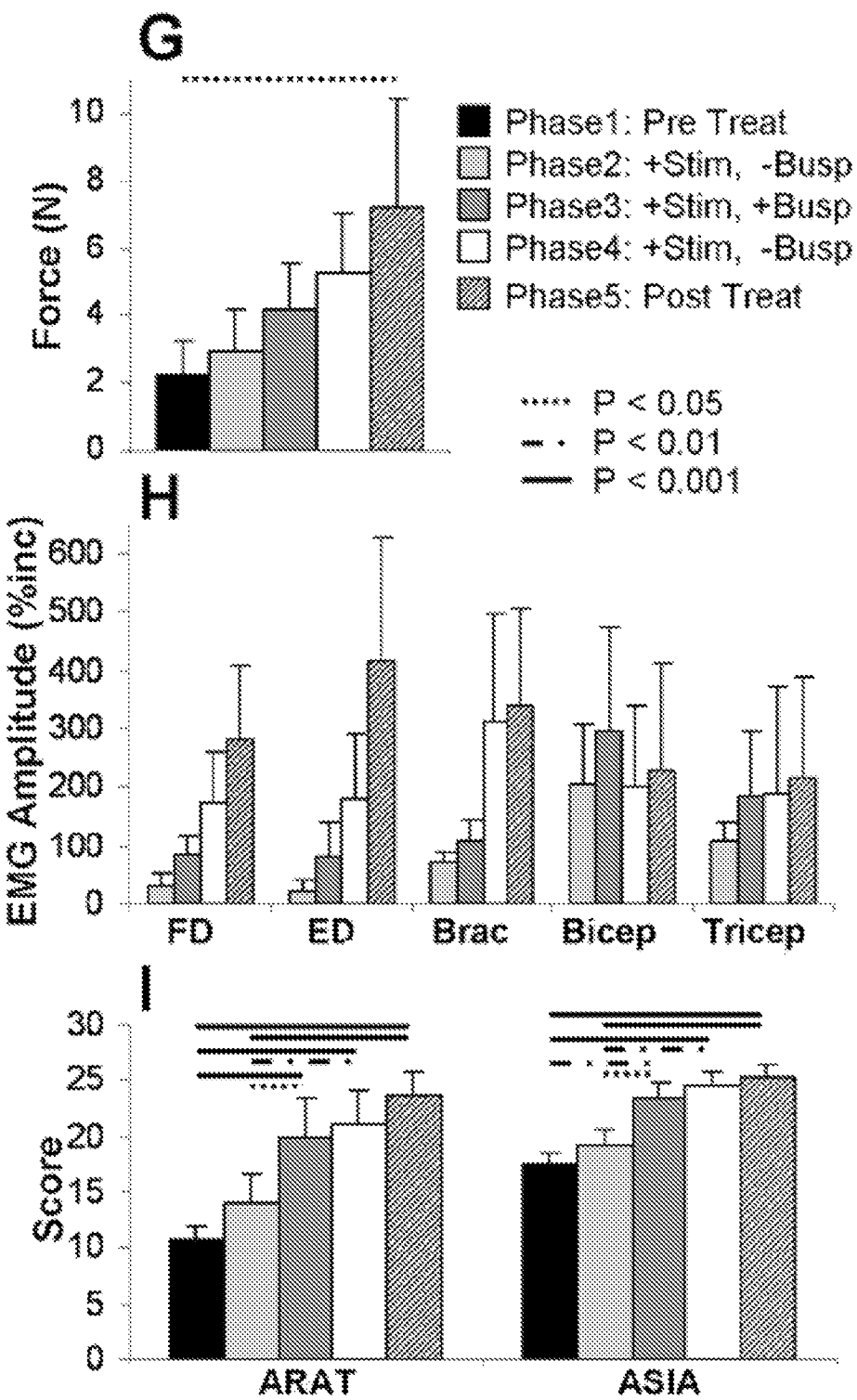
*Fig. 1, cont'd.*

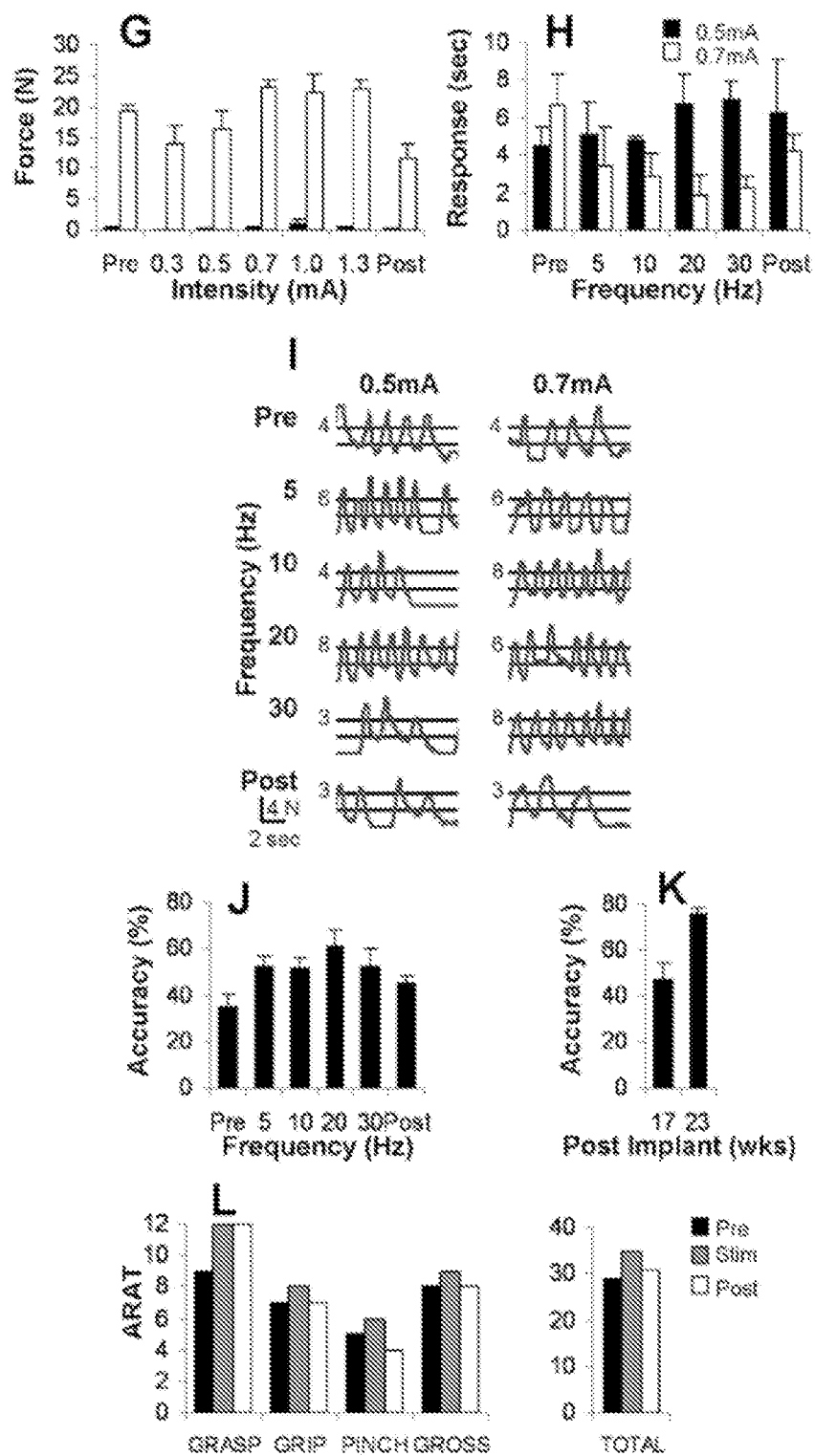
Fig. 2, cont'd.

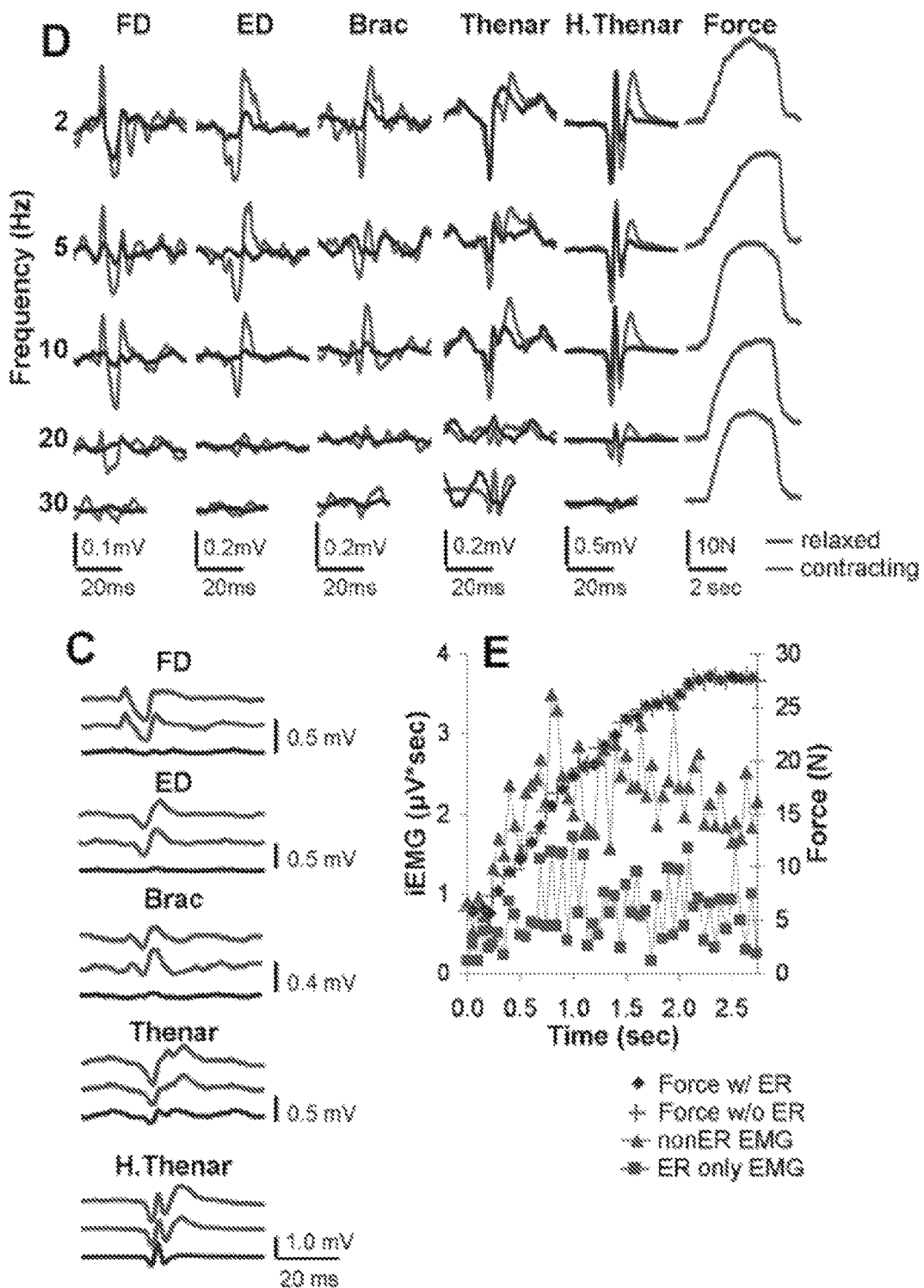
Fig. 3, cont'd.

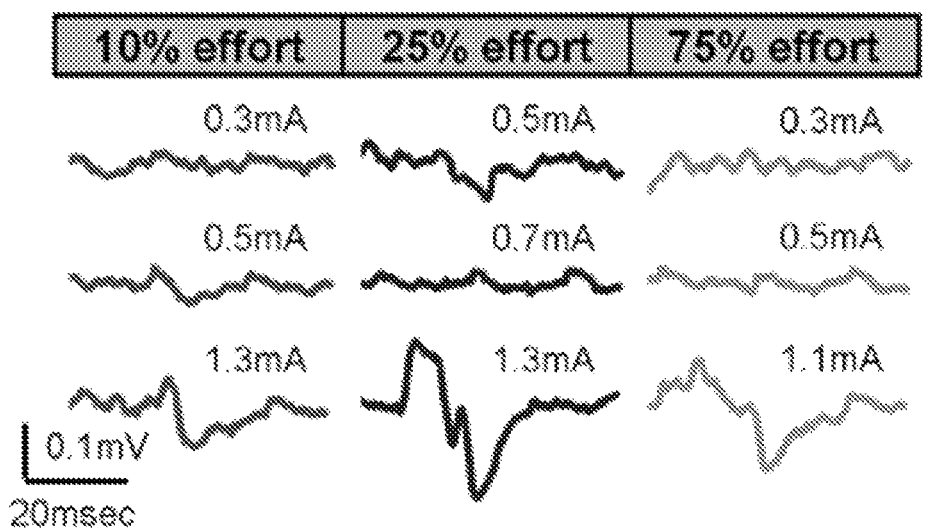
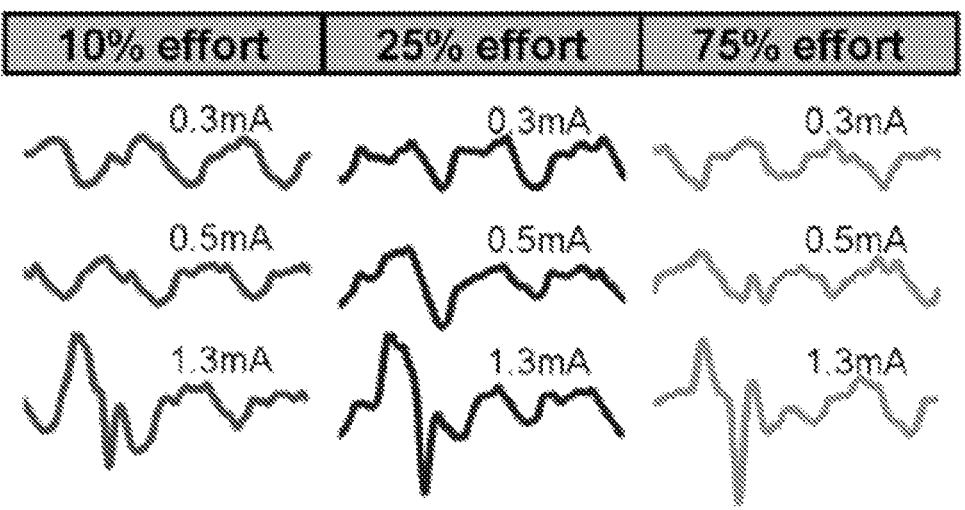
*Fig. 4, cont'd.*

| ASIA Upper Limb | | | | |
|---|---|---|---|---|
| | Beginning of Study | | Conclusion of Study | |
| | L | R | L | R |
| C5 | 3 | 4 | 5 | 5 |
| C6 | 1 | 1 | 4 | 4 |
| C7 | 0 | 0 | 3 | 3 |
| C8 | 0 | 0 | 2 | 2 |
| T1 | 0 | 0 | 2 | 2 |
| Total | 9 | | 32 | |

*Fig. 8*

ENGAGING THE CERVICAL SPINAL CORD CIRCUITRY TO RE-ENABLE VOLITIONAL CONTROL OF HAND FUNCTION IN TETRAPLEGIC SUBJECTS

CROSS-REFERENCE TO RELATED APPLICATIONS

This application is a 371 National Phase of PCT/US2014/057886, filed on Sep. 26, 2014, which claims benefit of and priority to U.S. Ser. No. 61/883,694, filed on Sep. 27, 2013, both of which are incorporated herein by reference in their entirety for all purposes.

STATEMENT OF GOVERNMENTAL SUPPORT

This invention was made with Government support under TR000124, awarded by the National Institutes of Health. The Government has certain rights in the invention.

BACKGROUND

Serious spinal cord injuries (SCI) affect approximately 1.3 million people in the United States, and roughly 12-15,000 new injuries occur each year. Of these injuries, approximately 50% are complete spinal cord injuries in which there is essentially total loss of sensory motor function below the level of the spinal lesion.

Paralysis of the upper limbs results in an enormous loss of independence of one's daily life. Meaningful improvement in hand function is generally rare after one year of tetraparesis.

SUMMARY

In various embodiments, methods are provided for applying spinal cord stimulation with and without selective pharmaceuticals to restore voluntary control of hand function in tetraplegic subjects. The spinal cord stimulation can be transcutaneous and/or epidural. In various embodiments the electrical stimulation alone or in combination with pharmaceuticals can be applied to facilitate restoration of motor control and/or force generation in subjects suffering with spinal cord injury and/or as other neurological injury and illness that effects motor control of the hand or paw. Successful application can provide a device for widespread use in rehabilitation of neurologic injury and disease.

In particular illustrative embodiments, the devices, optional pharmacological agents, and methods described herein stimulate the spinal cord with, e.g., electrodes that modulate the proprioceptive and supraspinal information that controls the hands during reaching and/or grasping and/or manipulating conditions. Without being bound by a particular theory, it is believed the proprioceptive and cutaneous sensory information guides the activation of the muscles in a coordinated manner and in a manner that accommodates the external conditions.

Unlike approaches that involve specific stimulation of motor neurons to directly induce a movement, the methods described herein can enable the spinal circuitry to control the movements. More specifically, the devices, optional pharmacological agents, and methods described herein can exploit the spinal circuitry and its ability to interpret proprioceptive information and to respond to that proprioceptive information in a functional way. In various embodiments, this is in contrast to other approaches where the actual movement is induced/controlled by direct stimulation (e.g., of particular motor neurons).

Accordingly, in various aspects, the invention(s) contemplated herein may include, but need not be limited to, any one or more of the following embodiments:

Embodiment 1: A method of improving motor control and/or strength in a hand of a subject with a neuromotor disorder affecting motor control of the hand, said method including: neuromodulating the cervical spinal cord of the subject by administering stimulation to the cervical spinal cord or a region thereof and by administering to the subject at least one monoaminergic agonist. In some instances of Embodiment 1, the spinal cord stimulation can be transcutaneous and/or epidural.

Embodiment 2: The method of embodiment 1, wherein said method includes administering transcutaneous stimulation to the cervical spinal cord or a region thereof.

Embodiment 3: The method of embodiment 1, wherein said method includes administering epidural stimulation to the cervical spinal cord or a region thereof.

Embodiment 4: The method of embodiment 1, wherein said method includes administering a monoaminergic agonist to said subject.

Embodiment 5: The method of embodiment 1, wherein said method includes administering transcutaneous stimulation to the cervical spinal cord or a region thereof in conjunction with administration of a monoaminergic agonist.

Embodiment 6: The method of embodiment 1, wherein said method includes administering epidural stimulation to the cervical spinal cord or a region thereof in conjunction with administration of a monoaminergic agonist.

Embodiment 7: The method of embodiment 1, wherein said method includes administering transcutaneous stimulation to the cervical spinal cord or a region thereof in conjunction with epidural stimulation of the cervical spinal cord or a region thereof.

Embodiment 8: The method of embodiment 1, wherein said method includes administering transcutaneous stimulation to the cervical spinal cord or a region thereof in conjunction with epidural stimulation of the cervical spinal cord or a region thereof in conjunction with administration of a monoaminergic agonist to said subject.

Embodiment 9: The method according to any one of embodiments 1, 2, 5, 7, and 8, wherein said transcutaneous stimulation is at a frequency ranging from about 3 Hz, or from about 5 Hz, or from about 10 Hz to about 100 Hz, or to about 80 Hz, or to about 40 Hz, or from about 3 Hz or from about 5 Hz to about 80 Hz, or from about 5 Hz to about 30 Hz, or to about 40 Hz, or to about 50 Hz.

Embodiment 10: The method according to any one of embodiments 1, 2, 5, and 7-9, wherein said transcutaneous stimulation is applied at an intensity ranging from about 10 mA to about 150 mA, or from about 20 mA to about 50 mA or to about 100 mA, or from about 20 mA or from about 30 mA, or from about 40 mA to about 50 mA, or to about 60 mA, or to about 70 mA or to about 80 mA.

Embodiment 11: The method according to any one of embodiments 1, 2, 5, and 7-10, wherein said transcutaneous stimulation is at a frequency and amplitude sufficient to improve hand strength and/or fine hand control.

Embodiment 12: The method according to any one of embodiments 1, 2, 5, and 7-11, wherein said transcutaneous stimulation is applied to the dorsal aspect of the neck in the area of C5.

Embodiment 13: The method according to any one of embodiments 1, 3, and 6-12, wherein said epidural stimulation is at a frequency ranging from about 3 Hz, or from about 5 Hz, or from about 10 Hz to about 100 Hz, or to about 80 Hz, or to about 40 Hz, or from about 3 Hz or from about 5 Hz to about 80 Hz, or from about 5 Hz to about 30 Hz, or to about 40 Hz, or to about 50 Hz.

Embodiment 14: The method according to any one of embodiments 1, 3, and 6-13, wherein said epidural stimulation is at an amplitude ranging from 0.05 mA to about 30 mA, or from about 0.1 mA to about 20 mA, or from about 0.1 mA to about 15 mA or to about 10 mA.

Embodiment 15: The method according to any one of embodiments 1, 3, and 6-14, wherein said pulse width ranges from about 150 μs to about 600 μs, or from about 200 μs to about 500 μs, or from about 200 μs to about 450 μs.

Embodiment 16: The method according to any one of embodiments 1, 3, and 6-15, wherein said epidural stimulation is at a frequency and amplitude sufficient to improve hand strength and/or fine hand control.

Embodiment 17: The method according to any one of embodiments 1, 3, and 6-16, wherein said epidural stimulation is applied paraspinally over vertebrae spanning C2 to T1.

Embodiment 18: The method according to any one of embodiments 1, 3, and 6-16, wherein said epidural stimulation is applied paraspinally over vertebrae spanning C5 to T1.

Embodiment 19: The method according to any one of embodiments 1, 3, and 6-18, wherein said epidural stimulation is applied via a permanently implanted electrode array.

Embodiment 20: The method of embodiment 19, wherein said electrode array is a parylene based microelectrode implant.

Embodiment 21: The method according to any one of embodiments 1, 4, 5, 6, and 8-20, wherein the at least one monoaminergic agonist includes a drug selected from the group consisting of a serotonergic drug, a dopaminergic drug, a noradrenergic drug, a GABAergic drug, and a glycinergic drug.

Embodiment 22: The method of embodiment 21, where the agent is selected from the group consisting of 8-hydroxy-2-(di-n-propylamino)tetralin (8-OH-DPAT), 4-(benzodioxan-5-yl)1-(indan-2-yl)piperazine (S15535), N-{2-[4-(2-methoxyphenyl)-1-piperazinyl]ethyl}-N-(2-pyridinyl)cyclo-hexanecarboxamide (WAY 100.635), Quipazine, Ketanserin, 4-amino-(6-chloro-2-pyridyl)-1 piperidine hydrochloride (SR 57227A), Ondanesetron, Buspirone, Methoxamine, Prazosin, Clonidine, Yohimbine, 6-chloro-1-phenyl-2,3,4,5-tetrahydro-1H-3-benzazepine-7,8-diol (SKF-81297), 7-chloro-3-methyl-1-phenyl-1,2,4,5-tetrahydro-3-benzazepin-8-ol (SCH-23390), Quinpirole, and Eticlopride.

Embodiment 23: The method of embodiment 21, wherein said monoaminergic agonist is buspirone.

Embodiment 24: The method of embodiment 22, wherein said drug is 8-hydroxy-2-(di-n-propylamino)tetralin (8-OH-DPAT).

Embodiment Embodiment 25: The method of embodiment 22, wherein said drug is 4-(benzodioxan-5-yl)1-(indan-2-yl)piperazine (S15535).

Embodiment 26: The method of embodiment 22, wherein said drug is N-{2-[4-(2-methoxyphenyl)-1-piperazinyl]ethyl}-N-(2-pyridinyl)cyclo-hexanecarboxamide (WAY 100.635).

Embodiment 27: The method of embodiment 22, wherein said drug is Quipazine.

Embodiment 28: The method of embodiment 22, wherein said drug is Ketanserin.

Embodiment 29: The method of embodiment 22, wherein said drug is 4-amino-(6-chloro-2-pyridyl)-1 piperidine hydrochloride (SR 57227A).

Embodiment 30: The method of embodiment 22, wherein said drug is Ondanesetron.

Embodiment 31: The method of embodiment 22, wherein said drug is Methoxamine.

Embodiment 32: The method of embodiment 22, wherein said drug is Prazosin.

Embodiment 33: The method of embodiment 22, wherein said drug is Clonidine.

Embodiment 34: The method of embodiment 22, wherein said drug is Yohimbine.

Embodiment 35: The method of embodiment 22, wherein said drug is 6-chloro-1-phenyl-2.

Embodiment 36: The method of embodiment 22, wherein said drug is 3,4,5-tetrahydro-1H-3-benzazepine-7.

Embodiment 37: The method of embodiment 22, wherein said drug is 8-diol (SKF-81297).

Embodiment 38: The method of embodiment 22, wherein said drug is 7-chloro-3-methyl-1-phenyl-1,2,4,5-tetrahydro-3-benzazepin-8-ol (SCH-23390).

Embodiment 39: The method of embodiment 21, wherein said drug is Quinpirole.

Embodiment 40: The method of embodiment 21, wherein said drug is and Eticlopride.

Embodiment 41: The method according to any one of embodiments 1 and 4-40, wherein a combination of transcutaneous and/or epidural stimulation and monoaminergic agonist provides a synergistic improvement in hand strength and/or fine hand control.

Embodiment 42: The method according to any one of embodiments 1-41, wherein said subject is a human. In some embodiments, the subject is a non-human mammal.

Embodiment 43: The method according to any one of embodiments 1-42, wherein said subject has a spinal cord injury.

Embodiment 44: The method of embodiment 43, wherein said spinal cord injury is clinically classified as motor complete.

Embodiment 45: The method of embodiment 43, wherein said spinal cord injury is clinically classified as motor incomplete.

Embodiment 46: The method according to any one of embodiments 1-42, wherein said subject has an ischemic brain injury.

Embodiment 47: The method of embodiment 46, wherein said ischemic brain injury is brain injury from stroke or acute trauma.

Embodiment 48: The method according to any one of embodiments 1-42, wherein said mammal has a neurodegenerative pathology.

Embodiment 49: The method of embodiment 48, wherein said neurodegenerative pathology is associated with a condition selected from the group consisting of Parkinson's disease, Huntington's disease, Alzheimer's disease, amyotrophic lateral sclerosis (ALS), primary lateral sclerosis (PLS), dystonia, and cerebral palsy.

Embodiment 50: The method according to any one of embodiments 1-49, wherein the stimulation is under control of the subject.

Embodiment 51: The method according to any one of embodiments 1-50, wherein said method further includes physical training of said subject.

Embodiment 52: The method of embodiment 51, wherein said physical training includes hand contraction against a resistance.

Embodiment 53: The method according to any one of embodiments 51-52, wherein said physical training includes tracing a displayed pattern by hand manipulation of a hand controller.

Embodiment 54: An electrical stimulator configured to induce epidural and/or transcutaneous electrical stimulation in the cervical region of a mammal according to any one of embodiments 1-20.

DEFINITIONS

As used herein "electrical stimulation" or "stimulation" means application of an electrical signal that may be either excitatory or inhibitory to a muscle or neuron and/or to groups of neurons and/or interneurons. It will be understood that an electrical signal may be applied to one or more electrodes with one or more return electrodes.

As used herein "epidural" means situated upon the dura or in very close proximity to the dura. The term "epidural stimulation" refers to electrical epidural stimulation. In certain embodiments epidural stimulation is referred to as "electrical enabling motor control" (eEmc).

The term "transcutaneous stimulation" or "transcutaneous electrical stimulation" or "cutaneous electrical stimulation" refers to electrical stimulation applied to the skin, and, as typically used herein refers to electrical stimulation applied to the skin in order to effect stimulation of the spinal cord or a region thereof. The term "transcutaneous electrical spinal cord stimulation" may also be referred to as "tSCS". The term "pcEmc" refers to painless cutaneous electrical stimulation.

The term "motor complete" when used with respect to a spinal cord injury indicates that there is no motor function below the lesion, (e.g., no movement can be voluntarily induced in muscles innervated by spinal segments below the spinal lesion.

The term "monopolar stimulation" refers to stimulation between a local electrode and a common distant return electrode.

The term "co-administering", "concurrent administration", "administering in conjunction with" or "administering in combination" when used, for example with respect to transcutaneous electrical stimulation, epidural electrical stimulation, and pharmaceutical administration, refers to administration of the transcutaneous electrical stimulation and/or epidural electrical stimulation and/or pharmaceutical such that various modalities can simultaneously achieve a physiological effect on the subject. The administered modalities need not be administered together, either temporally or at the same site. In some embodiments, the various "treatment" modalities are administered at different times. In some embodiments, administration of one can precede administration of the other (e.g., drug before electrical stimulation or vice versa). Simultaneous physiological effect need not necessarily require presence of drug and the electrical stimulation at the same time or the presence of both stimulation modalities at the same time. In some embodiments, all the modalities are administered essentially simultaneously.

BRIEF DESCRIPTION OF THE DRAWINGS

FIG. 8 shows upper extremity motor ASIA Impairment Score of Subject E. Motor function was assessed at the beginning and conclusion of the study, demonstrating a clinically significant 23-point increase during the study period.

DETAILED DESCRIPTION

Figure 1:
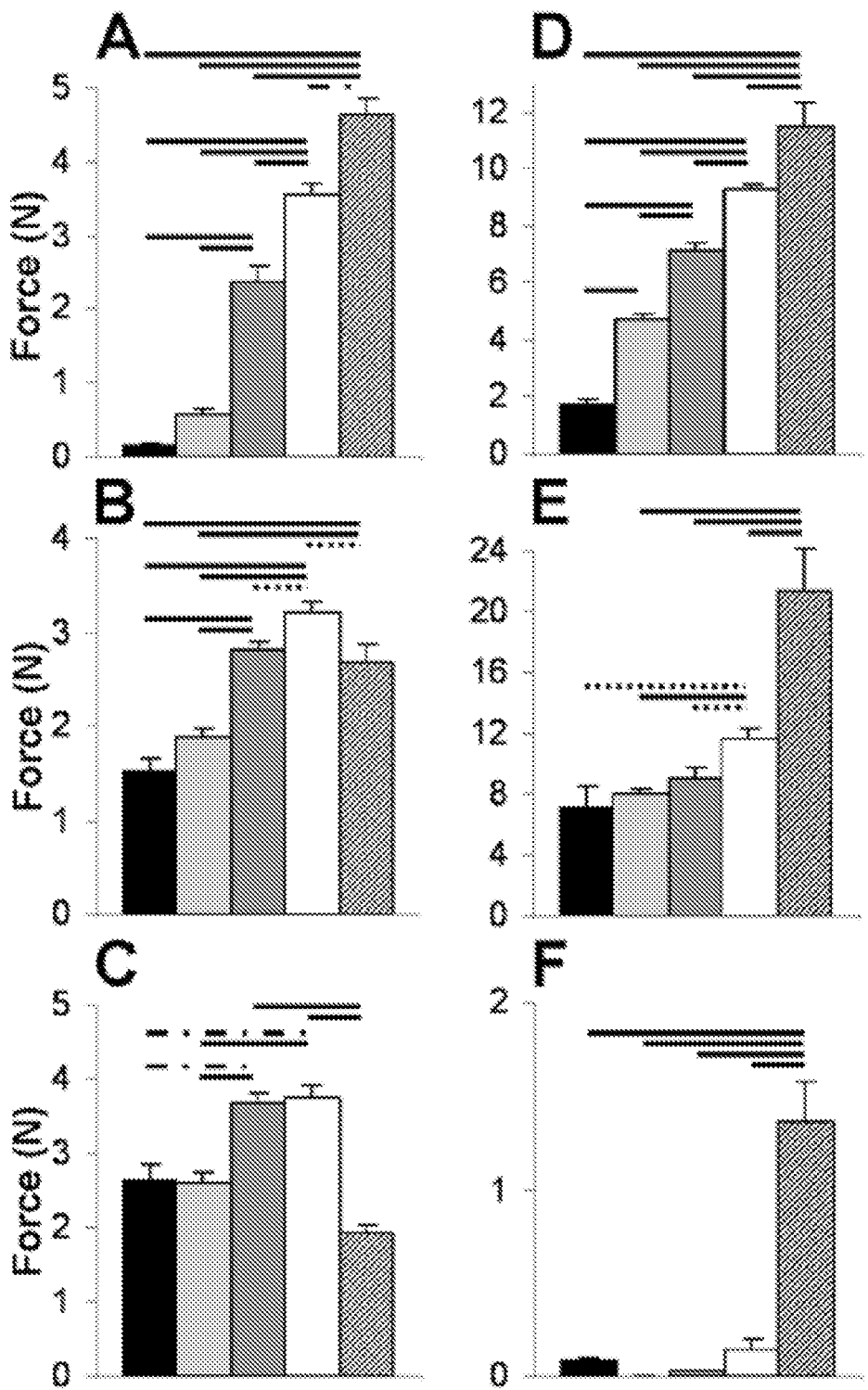
FIG. 1, panels A-I, illustrates improvement in hand function with interventions. Assessments of grip strength were made in 6 paralyzed subjects on 6 days of testing over 6 weeks Pre-Treatment (Phase 1, Pre Treat), followed by 4 days of testing over 2 weeks with pcEMC (Phase 2, +Stim, −Busp), followed by 4 days of testing over 2 weeks with pcEMC plus oral buspirone (Phase 3, +Stim, +Busp), followed by 4 days of testing over 2 weeks with pcEmc plus placebo (Phase 4, +Stim, −Busp), and followed by 4 days of testing over 2 weeks Post-Treatment after a 3-6 month delay (Phase 5, Post Treat) (Panels A-F). Mean (±SEM) grip strength for all 6 subjects (G), EMG amplitudes as percent increase over baseline (Pre Treat) levels (panel H), ARAT and upper extremity ASIA functional scores (panel I) are shown. Horizontal lines indicate significant differences at $P<0.05$, $P<0.01$, or $P<0.001$. FD, flexor digitorum; ED, extensor digitorum; Brac, brachioradialis; Bicep, biceps brachii; tricep, triceps brachii.

Embodiments described herein provide methods for applying spinal cord stimulation with and without selective pharmaceuticals to restore voluntary control of upper extremity function in tetraplegic subjects. In some embodiments, the upper extremity or extremities can be the hands. The spinal cord stimulation can be transcutaneous, epidural, or a combination thereof. The spinal cord stimulation alone or in combination with pharmaceuticals can be applied to facilitate restoration of motor control and/or force generation in individuals with spinal cord injuries.

As demonstrated herein in the Examples, an injured cervical spinal cord (e.g., a human cervical spinal cord) can be modulated using painless cutaneous electrical stimulation (pcEmc), monoaminergic agonist (fEmc) treatment, and/or eEmc to regain voluntary hand function. In some embodiments, mean hand strength can be increased by greater than 300% after pcEmc plus fEmc (buspirone) treatment. This was demonstrated in 6 subjects with a chronic motor complete cervical injury. One subject that was implanted with a cervical epidural electrode array realized significantly improved hand strength and fine hand control in the presence of cervical eEmc. Thus, the cervical circuitry can be neuromodulated to improve volitional control of hand function in tetraplegic subjects with one or more interventions: transcutaneous electrical stimulation (e.g., pcEMC), and/or monoaminergic agonist administration (fEmc), and/or epidural electrical stimulation (eEmc). In some embodiments, the impact of the herein described methods on individuals with upper limb paralysis can be dramatic functionally, psychologically, and economically.

Accordingly, in various embodiments, methods are provided for improving motor control and/or strength in a hand (or paw) of a subject with a neuromotor disorder affecting motor control of the hand (or paw). In various embodiments, the methods involve neuromodulating the cervical spinal cord of the subject by administering transcutaneous stimulation to the cervical spinal cord or a region thereof and/or neuromodulating the cervical spinal cord of said subject by administering epidural stimulation to the cervical spinal cord or a region thereof; and/or by administering to the subject a monoaminergic agonist (or other neuromodulatory pharmaceutical).

In some embodiments, neuromodulatory strategies can be used to improve fine motor control of the upper limbs, i.e., performance of motor tasks considered to be less "automatic" than posture and locomotion. These strategies can neuromodulate the lumbosacral spinal circuitry via epidural stimulation (electrical enabling motor control, eEmc)

In various embodiments, these methods can, optionally, be used in combination with physical training regimen. And in some embodiments, the pharmaceutical can be buspirone.

The methods described herein are for use with a mammal (e.g., a human, a mammal (e.g., a non-human primate, equine, feline, canus, etc.) who has a spinal cord with at least one dysfunctional spinal circuit that inhibits motor control and/or strength in a hand or paw and/or who exhibits another neuropathology that inhibits motor control and/or strength in a hand or paw. In one embodiment, the mammal is a human. As described herein, ranscutaneous electrical stimulation of the cervical spinal cord or a region thereof, and/or epidural stimulation of the cervical spinal cord, or a region thereof, and/or use of a neuromodulatory agent (e.g., a monoaminergic agent) can improve and/or restore motor control and/or strength to a hand or paw.

In some embodiments, hand function can be improved by neuromodulating the cervical spinal cord. Six subjects with chronic (18-36 months) spinal cord injury (SCI, traumatic cervical injury, ASIA B with no motor strength below the injury) were tested. All subjects initially had minimal hand strength, a condition characteristic of the majority of cervical SCI patients. The experimental approach began with six weeks of baseline testing (Phase 1), followed by three 2-week treatment periods (phases 2-4), and then by a period of approximately three months without any treatment at the end of which there was a final two week testing period (Phase 5). pcEmc at the C5 spinal segment (Phase 2) increased hand strength in 4/6 subjects compared to baseline Phase 1. During buspirone treatment (Phase 3), 4/6 subjects increased hand strength compared to Phase 1 and 2. The next 2 weeks buspirone was withdrawn but pcEmc continued (Phase 4), and again 4/6 subjects showed further improvement in grip strength compared to Phase 3. For all subjects combined, the mean grip strength tended to increase after each successive treatment phase. EMG amplitudes were generally consistent with increases in grip force, i.e., digit flexor and extensor EMG amplitudes tended to increase progressively across phases. After approximately three months without treatment, 4/6 subjects improved their performance relative to Phase 4.

These results show that the cervical spinal cord can be neuromodulated using two paradigms, i.e., electrically and pharmacologically. Moreover, these data indicate that non-functional networks can become engaged and progressively improve motor performance. In addition, the further improvement in hand function after withdrawing pcEMC and fEMC suggests that once functional connections are established they remain active.

Accordingly, the methods described herein are useful to improve and/or restore motor function to the hand or paw of a subject having paralysis affecting that hand or paw. In various embodiments, the methods provide that the spinal circuitry is neuromodulated to a physiological state that facilitates or enables the recovery or improved control of movement or improved strength of a hand or paw following some neuromotor dysfunction.

In some embodiments the paralysis effecting the hand or paw may be a motor complete paralysis or a motor incomplete paralysis. In certain embodiments the paralysis may have been caused by a spinal cord injury classified as motor complete or motor incomplete. The paralysis may have been caused by an ischemic or traumatic brain (or spinal) injury. In certain embodiments the paralysis may have been caused by an ischemic brain injury resulting from a stroke or acute trauma. By way of another example, the paralysis may have been caused by a neurodegenerative condition affecting the brain and/or spinal cord. In certain embodiments the neurodegenerative injury may be associated with a disease such as Parkinson's disease, Huntington's disease, Alzheimer's disease, frontotemporal dementia, dystonia, amyotrophic lateral sclerosis (ALS), primary lateral sclerosis (PLS), and other conditions such as cerebral palsy and multiple sclerosis (MS).

By way of non-limiting example, in certain embodiments, the methods described herein comprises application of electrical stimulation to the cervical spinal cord or a portion thereof of the subject. The electrical stimulation may be applied by a surface electrode(s) that is applied to the skin surface of the subject to provide a transcutaneous stimulation. Additionally, or alternatively, the electrical stimulation can be provided epidurally (e.g., via an implanted electrode or electrode array).

In various embodiments, the electrodes may; be implanted along, and/or the stimulation may be applied to the entire cervical spine (e.g., C1-T1) or to a region therein (e.g., C2-C7, C3-C7, C3-C6, C3-C5, C4-C7, C4-C6, C4-C5, C5, etc.). The electrical stimulation is delivered, e.g., as described herein (e.g., at 5-40 Hz at 20-100 mA). While not a requirement, the electrical stimulation may not directly activate muscle cells in the portion of the patient's body having the paralysis. In certain embodiments the electrodes (surface and/or implanted) may include an array of one or more electrodes stimulated in a monopolar biphasic configuration.

In various embodiments, the stimulation may include tonic stimulation and/or intermittent stimulation. The stimulation may include simultaneous or sequential stimulation, or combinations thereof, of different cord regions (e.g., different regions within the cervical spinal cord, or a region within the cervical spinal cord and another regions outside the cervical spinal cord). Optionally, in certain embodiments, the stimulation pattern may be under control of the subject.

In certain embodiments, the method(s) may include administering one or more neuropharmaceutical agents to the subject. The neuropharmaceutical agents may include, for example, a monoaminergic agent (e.g., buspirone).

In certain embodiments, the electrical stimulation is defined by a set of parameter values (e.g., frequency, amplitude, pulse width, etc.), and activation of the selected spinal circuit may (but need not) generate a quantifiable result. Optionally, the method may be repeated using electrical stimulation having different sets of parameter values to obtain quantifiable results generated by each repetition of the method. In certain embodiments a machine learning method may be executed by at least one computing device. The machine learning method builds a model of a relationship between the electrical stimulation applied to the spinal cord and the quantifiable results generated by activation of the at least one spinal circuit. A new set of parameters may be selected based on the model. By way of a non-limiting example, the machine learning method may implement a Gaussian Process Optimization, e.g., as described in PCT Publication No: WO/2012/094346 (PCT/US2012/020112).

In various embodiments, the methods described herein may further incorporate physical training In certain embodiments, the physical training may include inducing a resistance-providing positional change in the region of the subject where locomotor activity is to be facilitated (e.g., the hand and/or finger(s)). The positional change in the subject may include, but need not be limited to grasping and/or tracking. In certain embodiments, the physical training may include robotically guided training Another exemplary embodiment is a method that includes placing an electrode on the subject's cervical spinal cord, positioning the patient in a training device configured to assist with physical training that is configured to induce neurological signals in the hand or paw, and applying electrical stimulation to a portion of the cervical spinal cord of the subject.

Transcutaneous Stimulation of a Region of the Cervical Spine

The location of the electrode and its stimulation parameters are important in defining motor response. Use of surface electrode(s), as described herein, facilitates selection or alteration of particular stimulation sites as well as the application of a wide variety of stimulation parameters. Additionally surface stimulation can be used to optimize location for an implantable electrode or electrode array for epidural stimulation.

In various embodiments, the methods described herein involve transcutaneous electrical stimulation of the cervical spine or a region of the cervical spine of the subject. Illustrative regions include, but are not limited to one or more regions straddling or spanning a region selected from the group consisting of C1-C1, C1-C2, C1-C3, C1-C4, C1-C7, C1-C6, C1-C7, C1-T1, C2-C2, C2-C3, C2-C4, C2-C5, C2-C6, C2-C7, C2-T1, C3-C3, C3-C4, C3-C5, C3-C6, C3-C7, C3-T1, C4-C4, C4-C5, C4-C6, C4-C7, C4-T1, C5-C5, C5-C6, C5-C7, C5-T1, C6-C6, C6-C7, C6-T1, C7-C7, and C7-T1.

In certain embodiments, the stimulation is stimulation at a frequency ranging from about 3 Hz, or from about 5 Hz, or from about 10 Hz to about 100 Hz, or to about 80 Hz, or to about 40 Hz, or from about 3 Hz or from about 5 Hz to about 80 Hz, or from about 5 Hz to about 30 Hz, or to about 40 Hz, or to about 50 Hz.

In certain embodiments, the transcutaneous stimulation is applied at an intensity ranging from about 10 mA to about 150 mA, or from about 20 mA to about 50 mA or to about 100 mA, or from about 20 mA or from about 30 mA, or from about 40 mA to about 50 mA, or to about 60 mA, or to about 70 mA or to about 80 mA.

In certain embodiments, the transcutaneous stimulation is at a frequency and amplitude sufficient to improve hand strength and/or fine hand control when applied in conjunction with a neuromodulatory agent (e.g., a monoaminergic agent). In certain embodiments the transcutaneous stimulation is at a frequency and amplitude sufficient to improve hand strength and/or fine hand control when applied in conjunction with an epidural stimulation of the cervical spinal cord or a region thereof. In certain embodiments the transcutaneous stimulation is at a frequency and amplitude sufficient to improve hand strength and/or fine hand control when applied in conjunction with a neuromodulatory agent (e.g., a monoaminergic agent) and epidural stimulation of the cervical spinal cord or a region thereof. In certain embodiments the transcutaneous stimulation is at a frequency and amplitude sufficient to improve hand strength and/or fine hand control when utilized without epidural stimulation and/or without a neuromodulatory agent.

Epidural Stimulation of a Region of the Cervical Spine

In various embodiments, the methods described herein involve epidural electrical stimulation of the cervical spine or a region of the cervical spine of the subject. Illustrative regions include, but are not limited to, one or more regions straddling or spanning a region selected from the group consisting of C1-C1, C1-C2, C1-C3, C1-C4, C1-C7, C1-C6, C1-C7, C1-T1, C2-C2, C2-C3, C2-C4, C2-C5, C2-C6, C2-C7, C2-T1, C3-C3, C3-C4, C3-C5, C3-C6, C3-C7, C3-T1, C4-C4, C4-C5, C4-C6, C4-C7, C4-T1, C5-C5, C5-C6, C5-C7, C5-T1, C6-C6, C6-C7, C6-T1, C7-C7, and C7-T1.

In certain embodiments, the epidural stimulation is at a frequency ranging from about 3 Hz, or from about 5 Hz, or from about 10 Hz to about 100 Hz, or to about 80 Hz, or to about 40 Hz, or from about 3 Hz or from about 5 Hz to about 80 Hz, or from about 5 Hz to about 30 Hz, or to about 40 Hz, or to about 50 Hz.

In certain embodiments, the epidural stimulation is at an amplitude ranging from 0.05 mA to about 30 mA, or from about 0.1 mA to about 20 mA, or from about 0.1 mA to about 15 mA or to about 10 mA.

In certain embodiments, the pulse width ranges from about 150 μs to about 600 μs, or from about 200 μs to about 500 μs, or from about 200 μs to about 450 μs.

In certain embodiments, the epidural stimulation is at a frequency and amplitude sufficient to improve hand strength and/or fine hand control. In certain embodiments the epidural stimulation is applied paraspinally over a cervical region identified above (e.g., over vertebrae spanning C2 to T1, over vertebrae spanning C5 to T1, etc.).

In certain embodiments, the epidural stimulation is applied via a permanently implanted electrode array (e.g., a typical density electrode array, a high density electrode array, etc.).

In certain embodiments, the epidural electrical stimulation is administered via a high density epidural stimulating array (e.g., as described in PCT Publication No: WO/2012/094346 (PCT/US2012/020112). In certain embodiments, the high density electrode arrays are prepared using microfabrication technology to place numerous electrodes in an array configuration on a flexible substrate. In some embodiments, epidural array fabrication methods for retinal stimulating arrays can be used in the methods described herein (see, e.g., Maynard (2001) *Annu. Rev. Biomed. Eng.,* 3: 145-168; Weiland and Humayun (2005) *IEEE Eng. Med. Biol. Mag.,* 24 (5): 14-21, and U.S. Patent Publications 2006/0003090 and 2007/0142878). In various embodiments, the stimulating arrays comprise one or more biocompatible metals (e.g., gold, platinum, chromium, titanium, iridium, tungsten, and/or oxides and/or alloys thereof) disposed on a flexible material. Flexible materials can be selected from parylene A, parylene C, parylene AM, parylene F, parylene N, parylene D, other flexible substrate materials, or combinations thereof. Parylene has the lowest water permeability of available microfabrication polymers, is deposited in a uniquely conformal and uniform manner, has previously been classified by the FDA as a United States Pharmacopeia (USP) Class VI biocompatible material (enabling its use in chronic implants) (Wolgemuth, Medical Device and Diagnostic Industry, 22 (8): 42-49 (2000)), and has flexibility characteristics (Young's modulus ~4 GPa (Rodger and Tai (2005) *IEEE Eng. Med. Biology*, 24 (5): 52-57)), lying in between those of PDMS (often considered too flexible) and most polyimides (often considered too stiff). Finally, the tear resistance and elongation at break of parylene are both large, minimizing damage to electrode arrays under surgical manipulation. The preparation and parylene microelectrode arrays suitable for use in the epidural stimulation methods described herein is described in PCT Publication No: WO/2012/100260 (PCT/US2012/022257).

The electrode array may be implanted using any of a number of methods (e.g., a laminectomy procedure) well known to those of skill in the art.

In various embodiments, the arrays are operably linked to control circuitry that permits selection of electrode(s) to activate/stimulate and/or that controls frequency, and/or pulse width, and/or amplitude of stimulation. In various embodiments, the electrode selection, frequency, amplitude, and pulse width are independently selectable, e.g., at different times, different electrodes can be selected. At any time, different electrodes can provide different stimulation frequencies and/or amplitudes. In various embodiments, different electrodes or all electrodes can be operated in a monopolar mode and/or a bipolar mode, using constant current or constant voltage delivery of the stimulation.

In certain embodiments, the electrodes can also be provided with implantable control circuitry and/or an implantable power source. In various embodiments, the implantable control circuitry can be programmed/reprogrammed by use of an external device (e.g., using a handheld device that communicates with the control circuitry through the skin). The programming can be repeated as often as necessary.

Any present or future developed stimulation system capable of providing an electrical signal to one or more regions of the cervical spinal cord may be used in accordance with the teachings provided herein. In various embodiments, the system may comprise an external pulse generator. In other embodiments the system may comprise an implantable pulse generator to produce a number of stimulation pulses that are sent to the a region in proximity to the cervical spinal cord by insulated leads coupled to the spinal cord by one or more electrodes and/or an electrode array. In certain embodiments the one or more electrodes or one or more electrodes comprising the electrode array may be attached to separate conductors included within a single lead. Any known or future developed lead useful for applying an electrical stimulation signal in proximity to a subject's spinal cord may be used. For example, the leads may be conventional percutaneous leads, such as PISCES® model 3487A sold by Medtronic, Inc. In some embodiments, it may be desirable to employ a paddle-type lead.

Any known or future developed external or implantable pulse generator may be used in accordance with the teachings provided herein. For example, one internal pulse generator may be an ITREL® II or Synergy pulse generator available from Medtronic, Inc, Advanced Neuromodulation Systems, Inc.'s GENESIS™ pulse generator, or Advanced Bionics Corporation's PRECISION™ pulse generator. One of skill in the art will recognize that the above-mentioned pulse generators may be advantageously modified to deliver therapy in accordance with the teachings provided herein.

In certain embodiments systems can employ a programmer coupled via a conductor to a radio frequency antenna. This system permits attending medical personnel to select the various pulse output options after implant using radio frequency communications. While, in certain embodiments, the system employs fully implanted elements, systems employing partially implanted elements may also be used in accordance with the teachings provided herein.

In one illustrative, but non-limiting system, a control module is operably coupled to a signal generation module and instructs the signal generation module regarding the signal to be generated. For example, at any given time or period of time, the control module may instruct the signal generation module to generate an electrical signal having a specified pulse width, frequency, intensity (current or voltage), etc. The control module may be preprogrammed prior to implantation or receive instructions from a programmer (or another source) through any known or future developed mechanism, such as telemetry. The control module may include or be operably coupled to memory to store instructions for controlling the signal generation module and may contain a processor for controlling which instructions to send to signal generation module and the timing of the instructions to be sent to signal generation module. In various embodiments, leads are operably coupled to signal generation module such that a stimulation pulse generated by signal generation module may be delivered via electrodes.

While in certain embodiments, two leads are utilized, it will be understood that any number of one or more leads may be employed. In addition, it will be understood that any number of one or more electrodes per lead may be employed. Stimulation pulses are applied to electrodes (which typically are cathodes) with respect to a return electrode (which typically is an anode) to induce a desired area of excitation of electrically excitable tissue in a region of the cervical spine. A return electrode such as a ground or other reference electrode can be located on same lead as a stimulation electrode. However, it will be understood that a return electrode may be located at nearly any location, whether in proximity to the stimulation electrode or at a more remote part of the body, such as at a metallic case of a pulse generator. It will be further understood that any number of one or more return electrodes may be employed. For example, there can be a respective return electrode for each cathode such that a distinct cathode/anode pair is formed for each cathode.

The epidural electrode stimulation systems described herein are intended to be illustrative and non-limiting. Using the teachings provided herein, alternative epidural stimulation systems and methods will be available to one of skill in the art.

Use of Neuromodulatory Agents

In certain embodiments, the transcutaneous and/or epidural stimulation methods described herein are used in conjunction with various pharmacological agents, particularly pharmacological agents that have neuromodulatory activity (e.g., are monoamergic). In certain embodiments, the use of various serotonergic, and/or dopaminergic, and/or noradrenergic, and/or GABAergic, and/or glycinergic drugs is contemplated. These agents can be used in conjunction with epidural stimulation and/or transcutaneous stimulation and/or physical therapy as described above. This combined approach can help to put the spinal cord (e.g., the cervical spinal cord) in an optimal physiological state for controlling a range of hand movements.

In certain embodiments, the drugs are administered systemically, while in other embodiments, the drugs are administered locally, e.g., to particular regions of the spinal cord. Drugs that modulate the excitability of the spinal neuromotor networks include, but are not limited to combinations of noradrenergic, serotonergic, GABAergic, and glycinergic receptor agonists and antagonists.

Dosages of at least one drug or agent can be between about 0.001 mg/kg and about 10 mg/kg, between about 0.01 mg/kg and about 10 mg/kg, between about 0.01 mg/kg and about 1 mg/kg, between about 0.1 mg/kg and about 10 mg/kg, between about 5 mg/kg and about 10 mg/kg, between about 0.01 mg/kg and about 5 mg/kg, between about 0.001 mg/kg and about 5 mg/kg, or between about 0.05 mg/kg and about 10 mg/kg.

Drugs or agents can be delivery by injection (e.g., subcutaneously, intravenously, intramuscularly), orally, rectally, or inhaled.

Illustrative pharmacological agents include, but are not limited to, agonists and antagonists to one or more combinations of serotonergic: 5-HT1A, 5-HT2A, 5-HT3, and 5HT7 receptors; to noradrenergic alpha 1 and 2 receptors; and to dopaminergic D1 and D2 receptors (see, e.g., Table 1).

TABLE 1

Illustrative pharmacological agents.

| Name | Target | Action | Route | Typical Dose (mg/Kg) | Typical Range (mg/kg) |
|---|---|---|---|---|---|
| Serotonergic receptor systems | | | | | |
| 8-OHDPAT | 5-HT1A7 | Agonist | S.C. | 0.05 | 0.045-0.3 |
| Way 100.635 | 5-HT1A | Antagonist | I.P. | 0.5 | 0.4-1.5 |
| Quipazine | 5-HT2A/C | Agonist | I.P. | 0.2 | 0.18-0.6 |
| Ketanserin | 5-HT2A/C | Antagonist | I.P. | 3 | 1.5-6.0 |
| SR 57227A | 5-HT3 | Agonist | I.P. | 1.5 | 1.3-1.7 |
| Ondanesetron | 5-HT3 | Antagonist | I.P. | 3 | 1.4-7.0 |
| SB269970 | 5-HT7 | Antagonist | I.P. | 7 | 2.0-10.0 |
| Noradrenergic receptor systems | | | | | |
| Methoxamine | Alpha1 | Agonist | I.P. | 2.5 | 1.5-4.5 |
| Prazosin | Alpha1 | Antagonist | I.P. | 3 | 1.8-3.0 |
| Clonidine | Alpha2 | Agonist | I.P. | 0.5 | 0.2-1.5 |
| Yohimbine | Alpha2 | Antagonist | I.P. | 0.4 | 0.3-0.6 |
| Dopaminergic receptor systems | | | | | |
| SKF-81297 | D1-like | Agonist | I.P. | 0.2 | 0.15-0.6 |
| SCH-23390 | D1-like | Antagonist | I.P. | 0.15 | 0.1-0.75 |
| Quinipirole | D2-like | Agonist | I.P. | 0.3 | 0.15-0.3 |
| Eticlopride | D2-like | Antagonist | I.P. | 1.8 | 0.9-1.8 |

The foregoing methods are intended to be illustrative and non-limiting. Using the teachings provided herein, other methods involving transcutaneous electrical stimulation and/or epidural electrical stimulation and/or the use of neuromodulatory agents to improve motor control and/or strength of a hand or paw will be available to one of skill in the art.

EXAMPLES

The following examples are offered to illustrate, but not to limit the claimed invention.

Example 1

Engaging the Cervical Spinal Cord Circuitry to Re-Enable Volitional Control of Hand Function in Tetraplegic Patients The present Example demonstrates whether herein described neuromodulatory strategies can be used to improve fine motor control of the upper limbs, i.e., performance of motor tasks considered to be less "automatic" than posture and locomotion. Here we show that the injured human cervical spinal cord can be modulated using painless cutaneous electrical stimulation (pcEmc), monoaminergic agonist (fEmc) treatment, and/or eEmc to regain voluntary hand function. Mean hand strength increased greater than 300% after pcEmc plus fEmc (buspirone) treatment in 6 subjects with a chronic motor complete cervical injury. One subject that was implanted with a cervical epidural electrode array realized significantly improved hand strength and fine hand control in the presence of cervical eEmc. Thus, we now demonstrate that the cervical circuitry can be neuromodulated to improve volitional control of hand function in tetraplegic subjects with three novel interventions. The impact of these observations on individuals with upper limb paralysis could be dramatic functionally, psychologically, and economically.

Six subjects with chronic (18-36 months) spinal cord injury (SCI, traumatic cervical injury, ASIA B with no motor strength below the injury) were tested to determine if hand function can be improved by neuromodulating the cervical spinal cord. All subjects initially had minimal hand strength, a condition reflecting the majority of cervical SCI patients. Our experimental approach began with 6 weeks of baseline testing (Phase 1), followed by three 2-week treatment periods (Phases 2-4), and then by a period of approximately three months without any treatment at the end of which there was a final 2-week testing period (Phase 5). pcEmc at the C5 spinal segment (Phase 2) increased hand strength in 4/6 subjects compared to baseline Phase 1 (FIG. 1, panels A-G). During buspirone treatment (Phase 3), 4/6 subjects increased hand strength compared to Phase 1 and 2. The next 2 weeks buspirone was withdrawn but pcEmc continued (Phase 4), and again 4/6 subjects showed further improvement in grip strength compared to Phase 3. For all subjects combined, the mean grip strength tended to increase after each successive treatment phase (FIG. 1, panel G). EMG amplitudes were generally consistent with increases in grip force, i.e., digit flexor and extensor EMG amplitudes tended to increase progressively across phases (FIG. 1, panel H). After approximately three months without treatment, 4/6 subjects improved their performance relative to Phase 4.

These results show that the cervical spinal cord can be neuromodulated using two paradigms, i.e., electrically and pharmacologically. In some embodiments, the present methods are highly interactive and perhaps synergistic. Synergy and interactivity were observed in animal experiments. These data suggest that non-functional networks can become engaged and progressively improve motor performance. In some embodiments, further improvement in hand function after withdrawing pcEMC and fEMC can be a result of functional connections remaining active once they are established.

Figure 6:
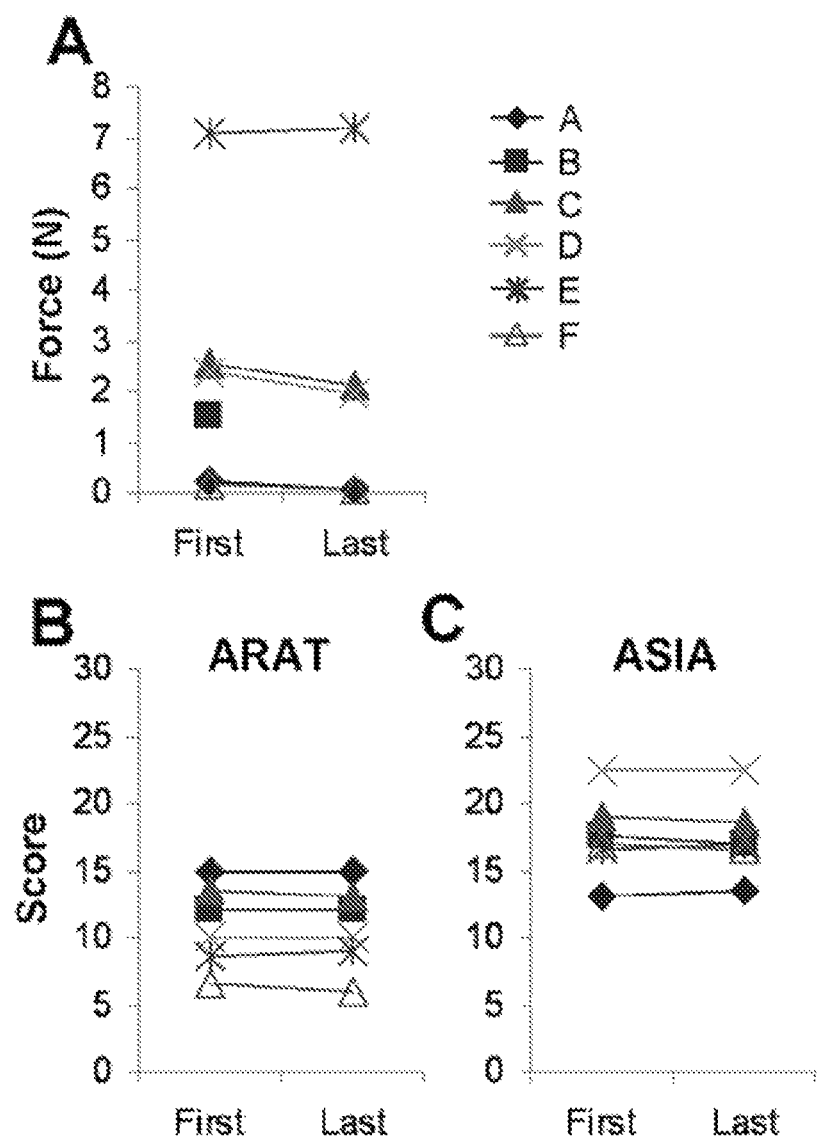
FIG. 6, panels A-C, shows that baseline testing (Phase 1) demonstrates stable hand function by handgrip device (panel A) and ARAT and ASIA scores (panel B) prior to initiation of any intervention. Maximal handgrip force on the last day of testing is not different from the first day of testing in the 6 subjects (panel A). Testing during this phase spanned a period of 6 weeks with bi-weekly testing sessions. Each data point represents an average of 3 maximal handgrip contractions. Clinical testing by ARAT and ASIA scores demonstrated no evidence of improvement during this initial baseline testing period (panel B).

The improvements are unlikely to be due to natural recovery or from repeated practice as large cohort studies of SCI patients have demonstrated that the majority of functional improvements occur within 6 months of the injury and that minimal recovery of function is observed past the 12 month time-point. All of our subjects were 18 months beyond the initial injury when recruited. Furthermore, baseline motor function testing for 6 weeks prior to any therapeutic intervention revealed stable function (FIG. 6). Concomitant to significantly improved hand strength, gains in upper extremity functional metrics by ARAT (13 point improvement) and ASIA (7 point improvement) tests, reflecting the impact of these interventions on the patient's overall upper extremity motor function (FIG. 1, panel I).

Figure 2:
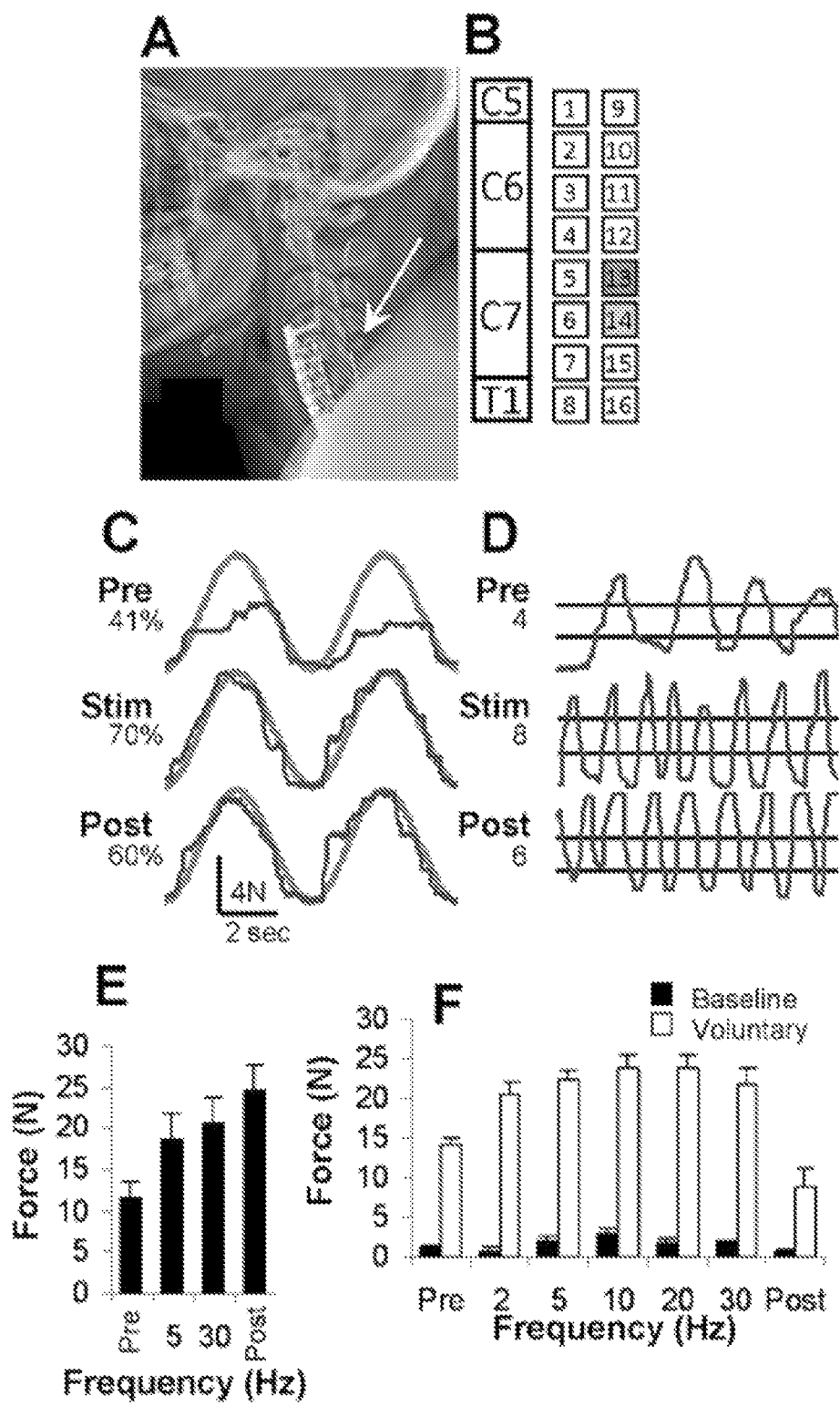
FIG. 2, panels A-L, shows motor performance relative to eEmc parameters. Subject E (C5 injury, ASIA panel B) was implanted with a 16-channel cervical epidural stimulation paddle array spanning spinal cord levels C5-T1, arrow pointing to electrode array (panels A and B). Prior to permanent implant, two parallel, temporary percutaneous linear electrodes were implanted. To assess hand control, the ability to accurately follow a targeted sign wave (panel C) and to perform rapid oscillations (panel D), and the maximal voluntary contraction (panel E) were determined during the initial day of eEmc before (Pre), during (Stim), and after (Post) stimulation (cathodes at C3 and anodes at T2, 30 Hz, 3.0 mA). After permanent paddle electrode implantation, stimulation at electrodes #13 and #14 (refer to schematic in panel B) was performed with the subject passive (Baseline) and when the subject attempted a voluntary contraction (Voluntary). Mean (±SEM, 3 trials for each condition) grip force during Baseline and Voluntary testing at varying stimulation frequencies (panel F) and intensities (panel G) are shown. Optimal stimulation parameters to affect hand function were assessed (panels H-J). Time to actuate the handgrip device (response time) was assessed at different stimulation frequencies and intensities (±SEM, 3 trials for each condition) (panel H). The parameter of 20 Hz, 0.7 mA elicited the shortest response time. Likewise, eEmc facilitated handgrip oscillation with doubling of oscillation ability compared to Pre and Post conditions of no stimulation (representative tracings shown) (panel I). Accuracy score during sinusoidal wave testing in response to varying frequencies of stimulation was assessed with the best scores observed at 20 Hz (±SEM, 3 trials for each condition) (panel J). Assessment of accuracy score over different sessions revealed chronic improvement with sinusoidal wave test (±SEM, 24 trials for each condition at electrode combinations of +13−14 and +13−6, 5-30 Hz, 0.7 mA) (panel K). These improvements in hand function in response to eEmc were evident in the acute improvements in clinical ARAT score with multi-site electrode combination (Stim) (70% at −12+3, 30% at −12+4, 5 Hz, 0.9 mA) (panel L). The improvement of 6 points in ARAT score reflects a clinically significant event. This 20% increase reflects improvements in all categories measured by ARAT and is above the minimal clinically important difference of 5.7 points established for this instrument (van der Lee et al. (2001) *J. Rehabil. Med.* 33: 110-113), demonstrating the relevance of this intervention in improving upper extremity function.
Figure 3:
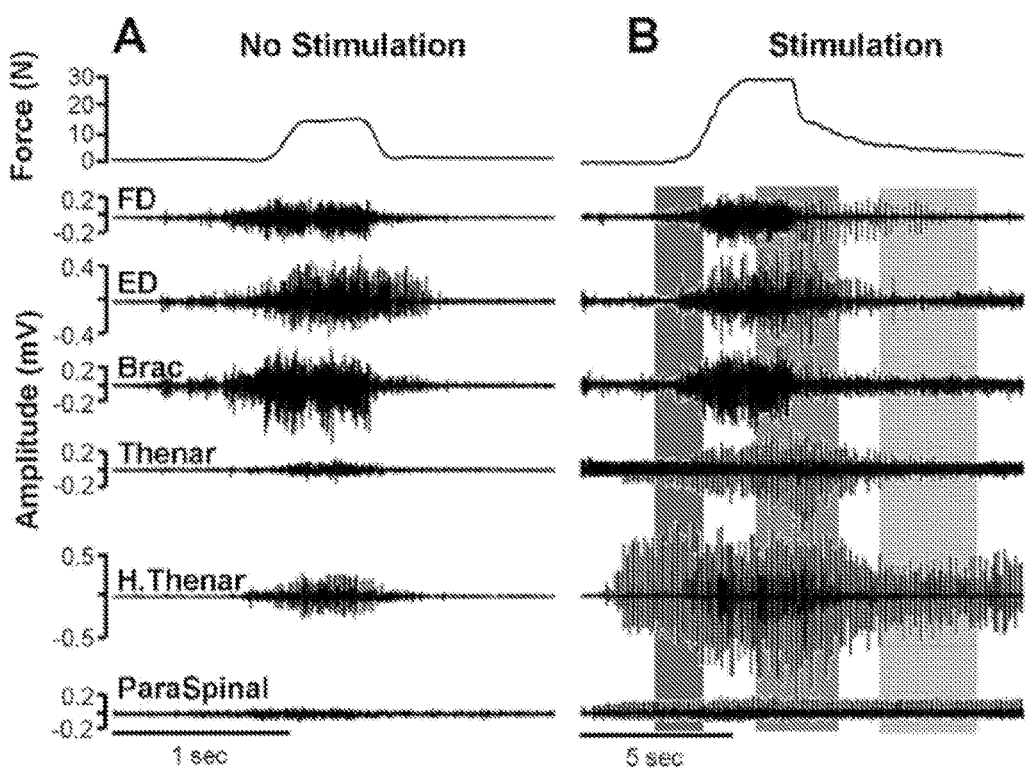
FIG. 3, panels A-E, shows hand grip force and evoked potentials in Subject E. Handgrip force and EMG during a maximum handgrip performed without (panel A) and with eEmc (panel B) of the cervical spinal cord (electrodes +13−14, 10 Hz, 1 mA). In (panel B), the initial stimulation phase without any voluntary effort (blue shaded area), the voluntary contraction phase (red shaded area), and the relaxation phase of the voluntary effort (green shaded area) are shown. At least twenty evoked potentials in each muscle were averaged during each phase. Note that an evoked potential was clearly evident in all muscles during the contraction and relaxation phases, but only in the H. thenar during the initial stimulation phase without any voluntary effort. The effect of frequency of stimulation on the average evoked potentials for 3 sec during the initial stimulation phase without any voluntary effort and during the voluntary contraction phase in each muscle are shown in panel C. The data demonstrate a substantially reduced evoked response in all muscles at the higher frequencies (20 and 30 Hz) during the voluntary contraction phase, but no substantial loss of force. The increase in force and two components of the EMG signal of the FD muscle during the initial phase of contraction is shown in panel E. The iEMG is divided into the energy (pV.sec) derived from evoked potentials synchronized with the stimulation pulses (20 Hz) and the total iEMG energy, i.e., the combination of the synchronized signals and that occurring randomly with respect to the stimulation pulses. The samples used for plotting the force are separated into those time bins when the EMG signals are largely alternating in amplitude. The + sign represents bins with the lowest amplitude and the triangles represent those with the highest amplitudes. The presence or absence of the lower synchronized signal had no impact on the force generated during a given time bin. H. Thenar, hypothenar; ER evoked response.
Figure 7:
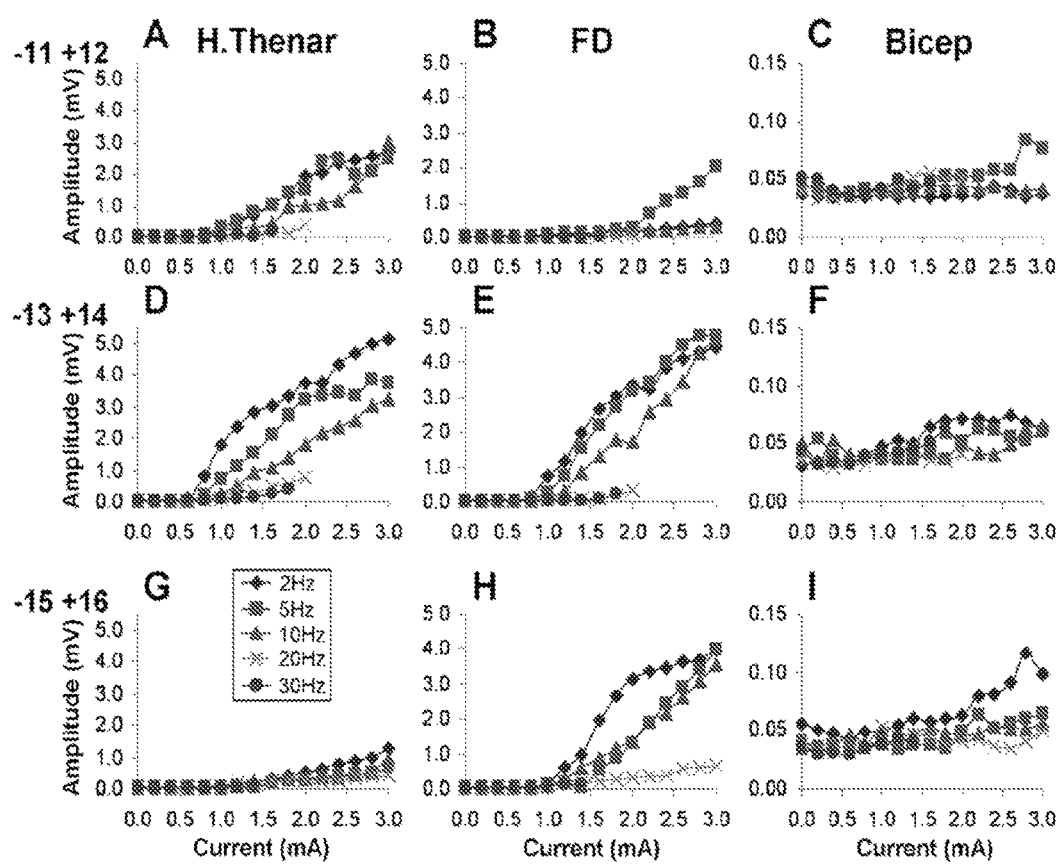
FIG. 7, panels A-I, show amplitudes of spinal cord evoked potentials induced by cathode-anode epidural electrode pairs with a range of currents and frequencies starting from the rostral to caudal spinal cord (refer to FIG. 2B for electrode configuration). The amplitude of the potentials demonstrates the relative responsiveness of each motor pool to the stimulation at a specific spinal location at a given level of current and frequency. The cathode-anode pair of −13+14 produced the most activation of muscles associated with hand function, i.e., H. Thenar and FD, and was used for most of the study.

Given the results above, we then asked whether the cervical spinal circuitry could be neuromodulated to improve hand function by stimulating via an epidural array implant (implanted in subject shown in FIG. 1, panel E). The implanted stimulating electrodes spanned the caudal portion of C5 to the rostral portion of T1 (FIG. 2, panel A, arrow; FIG. 2, panel B, electrode diagram). After mapping of the cervical motor pools by spinal cord evoked potentials (FIG. 7) we mainly used electrodes 13 and 14 to modulate hand function (FIG. 2, panel B, shaded boxes).

In the initial acute phase after implantation of a temporary trial array, the subject's ability to accurately follow a targeted force presented with a cursor moving in a sine wave pattern on a video screen was improved with eEmc (FIG. 2, panel C). The subject also could generate a more rapid oscillating force above and below a pre-selected target force in the presence of stimulation (FIG. 2, panel D). Additionally handgrip force was increased with stimulation at 5 and 30 Hz (FIG. 2, panel E). Importantly, some of these improvements were observed after stimulation.

After implantation of the permanent electrode array, we next performed a series of motor tests over the next 9 months comparing the effects of different stimulation parameters in facilitating maximum force and fine control. Maximal forces were generated at 10-20 Hz (FIG. 2, panel F) and 0.7-1.3 mA (FIG. 2, panel G). These forces were lower than the force generated in normal subjects (approximately 400 N), but substantially more than baseline. Evidence of the importance of selecting the optimal frequency and intensity of stimulation was reflected in the time that it took to respond to a signal to begin generating a force (FIG. 2, panel H). However, there were extremely long delays (sec) relative to uninjured subjects (approximately 200 ms) in voluntarily initiating a force regardless of the stimulation parameters. We compared the performance of these motor tasks to a commonly used clinical assessment tool and found a 6-point increase in ARAT with eEmc on vs. off during the same testing session, demonstrating the clinical relevance (FIG. 2, panel L).

Accuracy in controlling force was performed approximately weekly over a period of eight months to identify the optimal stimulation parameters. Rapid oscillatory movements were performed at 20 Hz and 0.5 mA and at 10 and 30 Hz and 0.7 mA (FIG. 2, panel I). Accuracy in following a targeted force occurred at 20 Hz (FIG. 2, panel J). In addition, the accuracy of controlling force in a sine wave pattern almost doubled over a two-month period (FIG. 2, panel K).

The present methods and systems provide that: 1) optimal stimulation parameters generating the highest forces differed from those generating the greatest accuracy at sub-maximal forces; 2) effects of stimulation intensity and frequency on maximum force production and accuracy are highly interdependent; 3) accuracy of force generation can be improved over time in the presence of eEmc; and 4) time needed to initiate a force following a command was prolonged, but could be improved with specific stimulation parameters. Each of these observations demonstrates the importance of matching the stimulation parameters with the task to be performed. In some embodiments, eEmc can yield improvement (e.g., meaningful) in upper extremity function in subjects with a cervical SCI.

Accuracy in controlling force was performed approximately weekly over a period of eight months to identify the optimal stimulation parameters. Rapid oscillatory movements were performed at 20 Hz and 0.5 mA and at 10 and 30 Hz and 0.7 mA (FIG. 2, panel I). Accuracy in following a targeted force occurred at 20 Hz (FIG. 2, panel J). In addition, the accuracy of controlling force in a sine wave pattern almost doubled over a two-month period (FIG. 2, panel K).

The present methods and systems provide that: 1) optimal stimulation parameters generating the highest forces differed from those generating the greatest accuracy at sub-maximal forces; 2) effects of stimulation intensity and frequency on maximum force production and accuracy are highly interdependent; 3) accuracy of force generation can be improved over time in the presence of eEmc; and 4) time needed to initiate a force following a command was prolonged, but could be improved with specific stimulation parameters. Each of these observations demonstrates the importance of matching the stimulation parameters with the task to be performed. In some embodiments, eEmc can yield improvement (e.g., meaningful) in upper extremity function in subjects with a cervical SCI.

Figure 4:
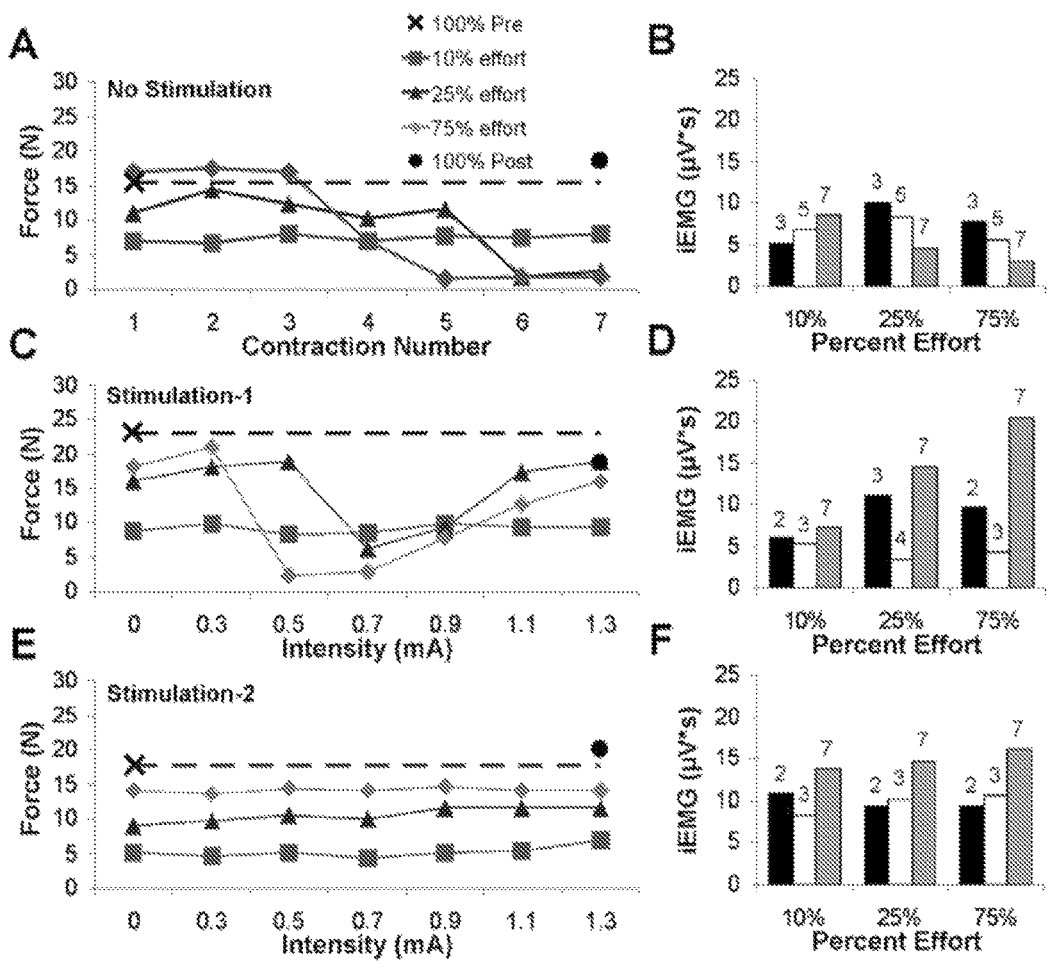
FIG. 4, panels A-H, shows handgrip forces and evoked responses at different % maximum efforts in Subject E. Handgrip force for a maximum contraction at the beginning of testing (100% Pre) followed by 7 consecutive contractions (5 sec between each contraction, and 5 min of rest between different efforts) at 10 (red), 25 (blue), 75 (green) % effort, and after 10 min of rest for a maximum contraction at the end of testing (100% Post) with no stimulation (A). The FD integrated EMG (iEMG) within this series of efforts is shown in (B). Numbers above the bars in (B), (D), and (F) are linked to the contraction numbers as labeled in (A). Fifteen min after the completion of (A), the same series of contractions were repeated in the presence of increasing intensities of stimulation ((C) and (D)). In this case, fatigue was evident at 0.7 and 0.5 mA when the subject was exerting 25 and 75% effort, respectively. Stimulation at the higher intensities enabled the subject to overcome substantial levels of fatigue. Additionally, there was an associated increase in iEMG compared to the initial contractions without fatigue as well as those in which fatigue occurred (D). To determine whether this fatigue effect was associated with repetitive contractions on the same day as in (A) and (C), on a separate day the same series of efforts at the same level of stimulation intensities were examined. In this case, there was no obvious fatigue (E) at any stimulation intensity as indicated by the constant forces and only minor increases in iEMG (F). The patterns of evoked potentials at selected percent efforts and at different strengths of stimulation when there was substantial fatigue and when there was no apparent fatigue is shown in (G) and (H), corresponding to iEMG (D) and (F), respectively. In spite of the absence of evidence of fatigue as indicated by the force with repeated contractions, to maintain that force may require higher intensities of stimulation to sustain the forces generated at the end of each series of contractions at a given percent effort (H). Stimulation parameters were electrode pattern of −13+14, 20 Hz, 0-1.3 mA.

A dysfunctional interaction may exist between supraspinal and sensory networks given the externally imposed neuromodulation of the spinal circuitry and since neither the descending motor control nor the spinal circuitry had functioned in any significant interactive way since the injury. This interaction was explored between supraspinally derived descending volitional drive and sensory-derived input to the spinal networks and motor pools when the spinal circuitry was being neuromodulated with eEmc. Could supraspinal networks volitionally accommodate the 'level of effort' to the level of motor pool excitability imposed by eEmc? To address this question we asked the subject to generate a series of seven contractions at different levels of maximum efforts with and without stimulation (FIG. 4). Without stimulation, the force level was maintained for all seven contractions at the lowest percentage effort, but force declined during the later contractions at the higher percentage efforts (FIG. 4, panel A). Over a wide range of stimulation intensities at the lowest percent effort, there were no marked differences in the subject's ability to estimate a target force (FIG. 4, panel C). At higher percent efforts fatigue was evident at moderate stimulation intensities, but this was overcome at the higher levels of stimulation, suggesting a neural deficit (FIG. 4, panels A and C). We repeated the experiments shown in FIG. 4, panels A and C (which occurred within 15 min period) on another day to avoid possible neuromuscular fatigue (FIG. 4, panel E). At the lower percent effort without stimulation, there was greater recruitment during the later contractions that enabled a constant force, whereas at the higher percent efforts the subject was unable to compensate with greater recruitment (FIG. 4, panel B). With stimulation, however, even at the higher efforts the targeted force could be reached as the result of greater motor pool excitation (FIG. 4, panel D). A similar but less dramatic change in excitation of the motor pools was present even when the targeted forces were reached at the different percent efforts (FIG. 4, panels D, F-H). In spite of the wide range in levels of neuromodulation there was remarkable consistency in volitionally generated forces. These results suggest that the subjects consciously perceived rather accurately the combined physiological state of supraspinal, spinal, and sensory networks to achieve the targeted levels of force simply defined conceptually as a "percent maximum effort" even in the presence of fatigue.

PcEmc, fEmc, and eEmc interventions can enhance the level of excitability of pre-motor spinal circuitries that mediate hand function. The importance of these data is that they identify three novel interventional strategies having significant potential for high clinical impact in a relatively short timeframe on a function considered to be of highest priority among paralyzed patients. The impact of these results is significant from the following perspectives: 1) neuromodulation is not dependent on the physiological phenomenon of central pattern generation but also applies to fine neuromotor control of less "automatic" movements; 2) they raise the possibility that the neuromodulatory concept could apply to other neural networks and therefore could be applied to neuromotor disorders such as stroke and Parkinson disease; and 3) they demonstrate the potential of enhancing maximum neuromuscular force, as well as fine control of movements. The improved force potential was associated with improved performance in upper extremity tasks (ARAT). Importantly, even after more than a year of inactivity of the sensorimotor circuits, significant levels of activity-dependent plasticity persist.

Methods Summary

The University of California, Los Angeles Institutional Review Board approved all procedures. Subjects were enrolled based on the enrollment criteria of traumatic cervical injury, ASIA B, greater than 1 year from injury, and stable motor function as documented by sequential clinical exams. Baseline clinical scores (ARAT, ASIA) prior to study intervention were assessed (FIG. 1, panel I).

Voluntary motor control data were assessed using a handgrip force measurement device. EMG data were collected via surface electrodes placed unilaterally on upper extremity muscles. Stimulation and data collection was obtained using the Konigsberg EMG system (Konigsberg, Pasadena, Calif.). Functional assessments by validated assessment tools were performed weekly during each study phase: American Spinal Injury Assessment (ASIA), and Action Research Arm Test (ARAT) (Carroll (1965) *J. Chronic Dis.*, 18: 479-491). Two blinded examiners conducted the functional tests.

The transcutaneous stimulation device is non-invasive. Stimulation parameters ranged from 5-30 Hz and 20-100 mA, located at C5. From the midpoint of Phase 1 to the end of Phase 4 all subjects were informed that they would receive either a placebo or the monoaminergic agonist (7.5 mg buspirone twice daily for 2 weeks beginning the day before biweekly testing). All subjects received buspirone during Phase 3 and a placebo during Phases 1, 2, and 4. All subjects and testers were blinded.

A temporary trial with two 16-contact percutaneous epidural leads (Linear Lead, Boston Scientific, Valencia, Calif.) spanning C2 to T1 was conducted prior to permanent implantation in one subject. Indication for implantation was for treatment of pain. Stimulation intensity ranged between 0.1-10.0 mA, frequencies ranged between 5-60 Hz, and pulse width was at 210 or 450 ps. After 7 days, one Boston Scientific Artisan (Valencia, Calif.) 16-electrode epidural array and one Boston Scientific Precision Plus Spinal Cord Stimulator (Valencia, Calif.) were implanted encompassing C5 to T1. The effects of various combinations of stimulation parameters were assessed to obtain the best response for hand function. Stimulation intensity ranged between 0.13.0 mA, frequencies ranged between 5-60 Hz, and pulse width was at 210 or 450 ps.

Outcomes were averaged across all observations in a given phase/period for each subject. Group mean changes across subjects in grip strength, EMG amplitude, ARAT score and ASIA score from baseline over the 5 phases were compared using a non-parametric repeated measure analysis of variance model using re-sampling. A two sided p value of $p<0.05$ was considered significant. Means±standard error of the mean (SEM) are reported.

Methods

Subject Profiles

Figure 5:
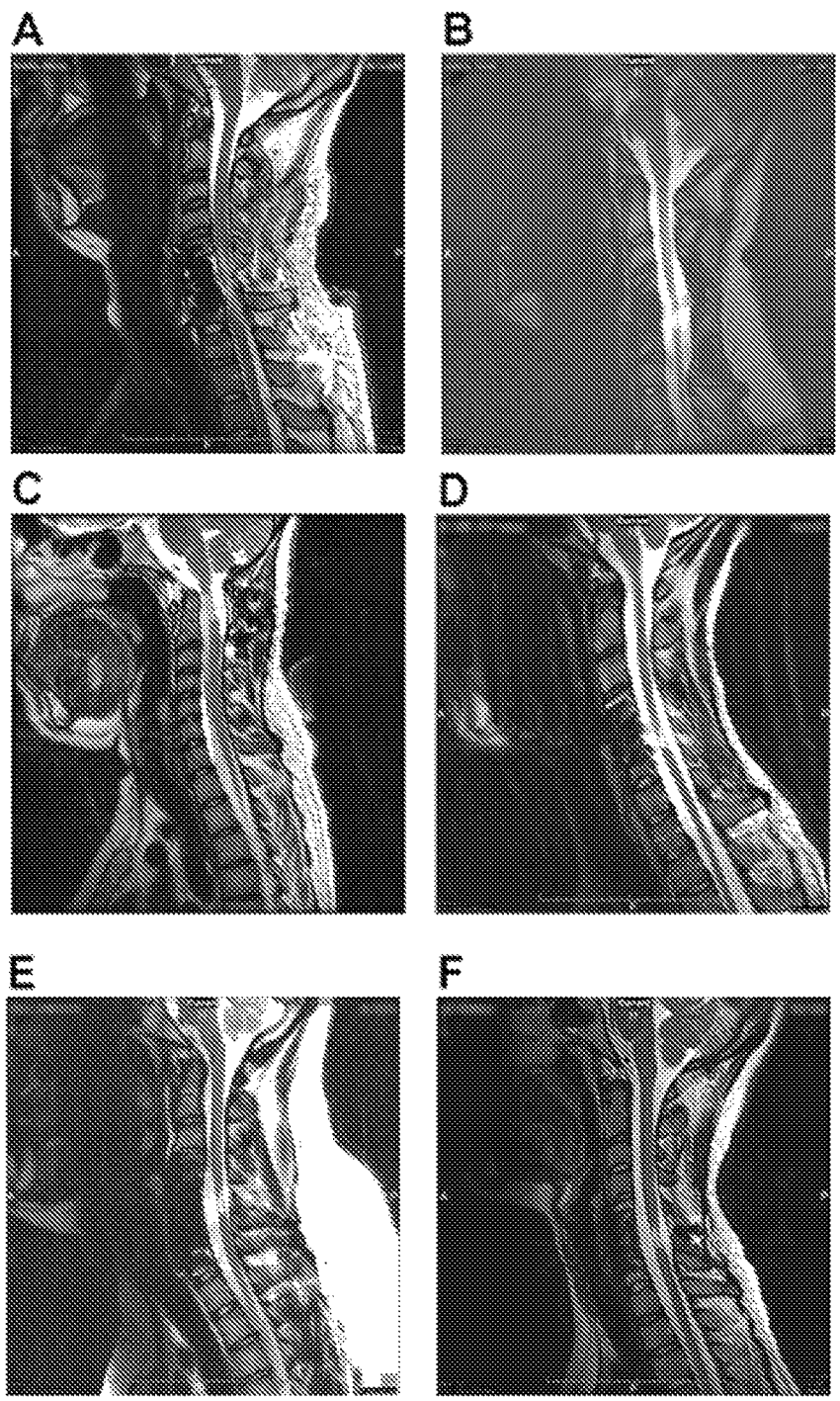
FIG. 5, panels A-F, shows sagittal T2 MRI Imaging demonstrating location of cervical spinal cord injury of subjects A-F, approximating C2 (panel C), C5 (panels B, D, E) or C6 (panels A, F) spinal cord segment. Normal tissue at injury location is replaced by a high intensity signal representing a glial scar. Spinal cord tissue distal and proximal to the injury locus is seen to be intact without evidence of post-traumatic syrinx formation or on-going compressive lesion.

The University of California, Los Angeles Institutional Review Board approved all procedures. Subjects were enrolled based on the enrollment criteria of traumatic cervical injury, ASIA B, greater than 1 year from injury, and stable motor function as documented by sequential clinical exams. The clinical profiles of the subjects upon enrollment into this study are as follows: Subject A was a 20 year old male who suffered a C6 SCI after a motor vehicle accident and was 36 months from initial injury; Subject B was a 18 year old male who suffered a C5 SCI after a diving accident and was 18 months from initial injury; Subject C was a 21 year old female who suffered a C2 SCI after a motor vehicle accident and was 45 months from initial injury; Subject D was a 20 year old male who suffered a C5 SCI sustained during football game and was 30 months from initial injury; Subject E was a 18 year old male who suffered a C5 SCI after a diving accident and was 24 months from initial injury; and Subject F was an 18 year old female with C6 SCI sustained after a fall from height and was 18 months from initial injury. Magnetic resonance imaging was obtained in all subjects to confirm location and description of injury (FIG. 5). Baseline clinical scores (ARAT, ASIA) were assessed prior to and throughout the study (FIG. 1, panel I).

Hand Testing

Voluntary motor control data were assessed using a handgrip force measurement device. Motor assessment was conducted on the arm that was most functional post-injury regardless of the pre-injury dominant side. Briefly, the device measures displacement against springs with a range in spring constants. Measurement of maximal voluntary contraction was conducted by asking the subject to contract his/her hand against the springs to maximally displace the handgrip. The contraction lasted for approximately 3-5 sec and was repeated twice. For hand oscillation/repeated contractions, the subject was asked to contract and release the hand as fast as possible above and below two lines on a computer screen that was preset at 12.5 and 37.5% of maximum voluntary contraction. The number of completed contraction-release sequences across the lines was determined. For hand control, the subject was asked to trace a sinusoidal wave (0.15 Hz) that appeared on the computer screen by squeezing the handgrip. The percentage of data points that fell inside a circular window at a sampling of 15 Hz was determined. The EMG data were collected via surface electrodes placed unilaterally on the biceps brachii (biceps), triceps brachii (triceps), brachioradialis (Brac), extensor digitorum (ED), flexor digitorum (FD), thenar, and hypothenar (H. Thenar) muscles. Stimulation and data collection was obtained using the Konigsberg EMG system (Konigsberg, Pasadena, Calif.). Functional assessments by validated assessment tools were performed weekly during each phase of study: American Spinal Injury Assessment (ASIA), and Action Research Arm Test (ARAT) (Carroll (1965) *J. Chronic Dis.*, 18: 479-491).

ARAT was selected due its focus on arm motor ability and because it has been validated and applied in the SCI setting. Scoring was conducted by two experienced examiners who were not informed of the treatment phase (blinded). If discrepancy existed between the scores, the exam was repeated and a consensus reached.

Prior to initiation of the study, the stability of hand function and training effect of utilizing the handgrip was assessed over the course of 6 weeks during which the subjects were tested and trained with the handgrip twice/week. In all subjects assessed, there was no improvement in hand function during this baseline testing (FIG. 6). Testing and training during this assessment period involved asking the subject to maximally contract the hand using the handgrip device. A total of 9-36 maximum hand contractions were performed during each session over a period of one to two hours.

pcEMC and fEMC

The transcutaneous stimulation device is non-invasive. A surface stimulation cathode electrode was attached on the dorsal aspect of the neck (C5 area) and the grounding electrode was placed on the anterior superior iliac spine. Stimulation parameters ranged from 5-30 Hz and 20-100 mA. Varying combinations of these stimulation parameters were systematically assessed to obtain optimum facilitation of voluntary hand contraction by identification of the relative activation levels of the motor pools studied (data not shown). During each of the three treatment periods (Phases 2-4) a series of nine 3.5-sec maximum hand grip strength tests were performed per treatment session. In each session of Phase 2, three contractions were performed without pcEmc, followed by three in the presence of pcEmc (twice weekly at 30 Hz and 20-40 mA), followed by three without pcEmc. The same pcEmc protocol was followed during Phases 2-4. The duration of pcEmc during each testing session was approximately 15-30 min. The total number of maximum hand contractions was 9-36 and each session lasted 1 to 2 hours. During pcEMC, the subjects reported a non-painful, tingling sensation down the arms at the higher stimulation intensities at the site of stimulation with some associated tonic paraspinal muscle contractions at the neck.

From the midpoint of the Phase 1 to the end of Phase 4 all subjects were informed that they would receive either a placebo or the monoaminergic agonist buspirone. All subjects and testers were blinded as to which treatment was administered and were given buspirone (7.5 mg buspirone twice daily for 2 weeks beginning the day before biweekly testing) during Phase 3 and a placebo during Phases 1, 2, and 4.

eEMC

Planning for surgical placement of spinal cord epidural stimulator (eEmc) on subject E was initiated prior to study enrollment. The criteria for selection was based on Federal Drug Administration approved use for the treatment of pain and Dr. Lu and two other physicians confirmed the indication for implantation. A temporary trial with two 16-contact percutaneous epidural leads (Linear Lead, Boston Scientific, Valencia, Calif.) spanning C2 to T1 was conducted prior to permanent implantation. After implantation, testing was conducted over a 2-hour session to assess the efficacy for improving hand function. Stimulation amplitude ranged between 0.110.0 mA, frequencies ranged between 5-60 Hz, and pulse width was at 210 or 450 ps. Total time of stimulation was 30 min.

After 7 days of confirmed efficacy in the treatment of pain, one Boston Scientific Artisan (Valencia, Calif.) 16-electrode epidural array and one Boston Scientific Precision Plus Spinal Cord Stimulator (Valencia, Calif.) were implanted encompassing C5 to T1. The effects of various combinations of stimulation parameters were assessed to obtain the best response for hand function. A combined total of 60 testing sessions were conducted on Subject E over the course of 20 months (epidural implant occurred between testing session 21 and 22). Each testing session lasted up to 180 min. During each testing session, stimulation duration lasted between 30-120 min. Stimulation amplitude ranged between 0.1-3.0 mA, frequencies ranged between 5-60 Hz, and pulse width was at 210 or 450 ps. During low intensity eEMC, the subject reported a tingling sensation at the neck that migrated toward the arms and hands. At the optimal stimulation parameters, the subject reported the perception of increased hand strength and control similar to pre-injury ability.

Statistical Analysis

Outcome measures (grip strength force, EMG amplitude, ARAT score, ASIA score) were averaged across all observations in a given Phase for each subject. Using these values, group mean changes across subjects for each outcome measure from baseline over the 5 phases were compared using a non-parametric repeated measure analysis of variance model using re-sampling (bootstrap). The repeated measure mixed model takes into account the correlation across time on the same subjects. A two-sided p value of $p<0.05$ was considered significant. Standard error of the mean (SEM) are reported. Individual mean profiles and the corresponding within person SEM also are reported.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of improving motor control and/or strength in a hand of a subject with a neuromotor disorder affecting motor control of the hand, said method comprising:
   neuromodulating a cervical spinal cord of said subject by administering transcutaneous stimulation to the cervical spinal cord or a region thereof; and/or
   neuromodulating the cervical spinal cord of said subject by administering epidural stimulation to the cervical spinal cord or a region thereof; and/or
   by administering to said subject at least one monoaminergic agonist: and wherein said method additionally comprises physical training of said subject where said physical training comprises:
   hand contraction against a resistance: and/or
   tracing a displayed pattern by hand manipulation of a hand controller.

2. The method of claim 1, wherein said method comprises administering transcutaneous stimulation or epidural stimulation to the cervical spinal cord or a region thereof.

3. The method of claim 1, wherein said method comprises administering a monoaminergic agonist to said subject.

4. The method of claim 1, wherein said method comprises administering transcutaneous or epidural stimulation to the cervical spinal cord or a region thereof in conjunction with administration of a monoaminergic agonist.

5. The method of claim 1, wherein said method comprises administering transcutaneous stimulation to the cervical spinal cord or a region thereof in conjunction with epidural stimulation of the cervical spinal cord or a region thereof.

6. The method of claim 1, wherein said method comprises administering transcutaneous stimulation to the cervical spinal cord or a region thereof in conjunction with epidural stimulation of the cervical spinal cord or a region thereof in conjunction with administration of a monoaminergic agonist to said subject.

7. The method of claim 1, wherein:
said transcutaneous stimulation is at a frequency ranging from about 3 Hz, or from about 5 Hz, or from about 10 Hz to about 100 Hz, or to about 80 Hz, or to about 40 Hz, or from about 3 Hz or from about 5 Hz to about 80 Hz, or from about 5 Hz to about 30 Hz, or to about 40 Hz, or to about 50 Hz; and/or
said epidural stimulation is at a frequency ranging from about 3 Hz, or from about 5 Hz, or from about 10 Hz to about 100 Hz, or to about 80 Hz, or to about 40 Hz, or from about 3 Hz or from about 5 Hz to about 80 Hz, or from about 5 Hz to about 30 Hz, or to about 40 Hz, or to about 50 Hz.

8. The method of claim 1, wherein:
said transcutaneous stimulation is applied at an intensity ranging from about 10 mA to about 150 mA, or from about 20 mA to about 50 mA or to about 100 mA, or from about 20 mA or from about 30 mA, or from about 40 mA to about 50 mA, or to about 60 mA, or to about 70 mA or to about 80 mA; and/or
said epidural stimulation is at an amplitude ranging from 0.05 mA to about 30 mA, or from about 0.1 mA to about 20 mA, or from about 0.1 mA to about 15 mA or to about 10 mA.

9. The method of claim 1, wherein said transcutaneous stimulation and/or epidural stimulation is at a frequency and amplitude sufficient to improve hand strength and/or fine hand control.

10. The method of claim 1, wherein transcutaneous stimulation is applied to a dorsal aspect of a neck in an area of C5.

11. The method according of claim 1, wherein said stimulation comprise a signal having a pulse width that ranges from about 150 µs to about 600 µs, or from about 200 µs to about 500 µs, or from about 200 µs to about 450 µs.

12. The method of claim 1, wherein said transcutaneous stimulation and/or said epidural stimulation is applied paraspinally over vertebrae spanning C2 to T1.

13. The method of claim 1, wherein epidural stimulation is applied via a permanently implanted electrode array.

14. The method of claim 1, wherein said method comprises administering to said subject at least one monoaminergic agonist that comprises an agent selected from a group consisting of a serotonergic drug, a dopaminergic drug, a noradrenergic drug, a GABAergic drug, and a glycinergic drug.

15. The method of claim 14, wherein said agent is selected from a group consisting of 8-hydroxy-2-(di-n-propylamino) tetralin (8-OH-DPAT), 4-(benzodioxan-5-yl)1-(indan-2-yl) piperazine (S15535), N-{2-[4-(2-methoxyphenyl)-1-piperazinyl]ethyl}-N- (2-pyridinyl)cyclo-hexanecarboxamide (WAY 100.635), Quipazine, Ketanserin, 4-amino-(6-chloro-2-pyridyl)-1 piperidine hydrochloride (SR 57227A), Ondanesetron, Buspirone, Methoxamine, Prazosin, Clonidine, Yohimbine, 6-chloro-1-phenyl-2,3,4,5-tetrahydro-IH-3-benzazepine-7,8-diol (SKF-81297), 7-chloro-3-methyl-1-phenyl-1,2,4,5-tetrahydro-3-benzazepin-8-ol (SCH-23390), Quinpirole, and Eticlopride.

16. The method of claim 1, wherein a combination of transcutaneous and/or epidural stimulation and monoaminergic agonist provides a synergistic improvement in hand strength and/or fine hand control.

17. The method of claim 1, wherein said subject is a human.

18. The method of claim 1, wherein said subject has a spinal cord injury, or an ischemic brain injury, or a neurodegenerative pathology.

19. The method of claim 18, wherein said subject has a spinal cord injury that is clinically classified as motor complete or that is clinically classified as motor incomplete.

20. The method of claim 18, wherein said subject has an ischemic brain injury that is brain injury from stroke or acute trauma.

21. The method of claim 18, wherein said subject has a neurodegenerative pathology that is associated with a condition selected from a group consisting of Parkinson's disease, Huntington's disease, Alzheimer's disease, amyotrophic lateral sclerosis (ALS), primary lateral sclerosis (PLS), dystonia, and cerebral palsy.

22. The method of claim 1, wherein the stimulation is under control of the subject.

* * * * *